United States Patent
Slukvin et al.

(10) Patent No.: US 10,260,047 B2
(45) Date of Patent: Apr. 16, 2019

(54) ANGIOHEMATOPOIETIC PROGENITOR CELLS

(71) Applicant: Wisconsin Alumni Research Foundation, Madison, WI (US)

(72) Inventors: Igor I. Slukvin, Verona, WI (US); Maksym A. Vodyanyk, Madison, WI (US); Kyung-Dal Choi, Falcon Heights, MN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/955,760

(22) Filed: Dec. 1, 2015

(65) Prior Publication Data

US 2016/0194610 A1 Jul. 7, 2016

Related U.S. Application Data

(63) Continuation of application No. 13/590,591, filed on Aug. 21, 2012, now abandoned.

(60) Provisional application No. 61/526,520, filed on Aug. 23, 2011.

(51) Int. Cl.
| | | |
|---|---|---|
| *A61K 35/12* | (2015.01) | |
| *A61K 35/28* | (2015.01) | |
| *C12N 5/071* | (2010.01) | |
| *C12N 5/0789* | (2010.01) | |
| *G01N 33/50* | (2006.01) | |

(52) U.S. Cl.
CPC ............ *C12N 5/0692* (2013.01); *A61K 35/28* (2013.01); *C12N 5/0647* (2013.01); *G01N 33/502* (2013.01); *G01N 33/5073* (2013.01); *A61K 2035/124* (2013.01); *C12N 2502/1394* (2013.01); *C12N 2506/02* (2013.01); *C12N 2506/45* (2013.01)

(58) Field of Classification Search
None
See application file for complete search history.

(56) References Cited

U.S. PATENT DOCUMENTS

| | | |
|---|---|---|
| 7,615,374 B2 | 11/2009 | Slukvin et al. |
| 7,811,821 B2 | 10/2010 | Slukvin et al. |
| 8,034,613 B2 | 10/2011 | Slukvin et al. |
| 8,133,732 B2 | 3/2012 | Slukvin et al. |
| 8,158,422 B2 | 4/2012 | Slukvin et al. |
| 8,183,038 B2 | 5/2012 | Slukvin et al. |
| 2008/0233610 A1 | 9/2008 | Slukvin et al. |
| 2010/0015705 A1 | 1/2010 | Slukvin et al. |
| 2010/0081199 A1 | 4/2010 | Slukvin et al. |
| 2010/0261274 A1 | 10/2010 | Slukvin et al. |
| 2012/0040362 A1 | 2/2012 | Slukvin et al. |
| 2012/0142106 A1 | 6/2012 | Slukvin et al. |

OTHER PUBLICATIONS

Wu et al. "Hemogenic endothelial progenitor cells isolated from human umbilical cord blood." Stem Cells 25(11): 2770-2776, 2007.*
Vodyanik, M.A., Thomson, J.A., and Slukvin, II (2006). Leukosialin (CD43) defines hematopoietic progenitors in human embryonic stem cell differentiation cultures. Blood 108, 2095-2105.
Vodyanik, Maxim A., et al.: "A Mesoderm-derived Precursor for Mesenchymal Stem and Endothelial Cells"; Cell Stem Cell, Dec. 3, 2010, vol. 7, No. 6, Dec. 3, 2010 (Dec. 3, 2010), pp. 718-729, XP28184582, ISSN: 1875-9777. Entire article.
Choi, Kyung-Dal, et al.: Identification of Hemogenic Endothelium and Its Direct Precursor in Human Embryonic Stem Cell Differentiation Cultures:, BLOOD, vol. 118, No. 21, Nov. 2011 (Nov. 2011), pp. 569-570, XP55047786. Entire article.
Choi, Kyung-Dal, et al.: "Identification of The Hemogenic Endothelial Progenitor and Its Direct Precursor in Human Pluripotent Stem Cell Differentiation Cultures.", Cell Reports, Sep. 27, 2012, vol. 2, No. 3, Sep. 27, 2012 (Sep. 27, 2012), pp. 553-567, XP55047737, ISSN: 2211-1247. Entire article.
International Search Report; dated Dec. 21, 2012.

* cited by examiner

*Primary Examiner* — Emily A Cordas
(74) *Attorney, Agent, or Firm* — Quarles & Brady LLP

(57) ABSTRACT

A purified human cell population of subsets of angiohematopoietic progenitor cells, wherein the population is at least 94% pure and wherein the cells are selected with cell markers selected from the group of KDR, APLNR, VE-cadherin, PDGFRα, CD31, CD235a, CD73, CD43, and CD41a.

4 Claims, 16 Drawing Sheets
(12 of 16 Drawing Sheet(s) Filed in Color)

Specification includes a Sequence Listing.

Fig. 12A
A+P+ PM; EMHlin-APLNR+PDGFRα+
Day 3     Day 6     Day 9     Day 12
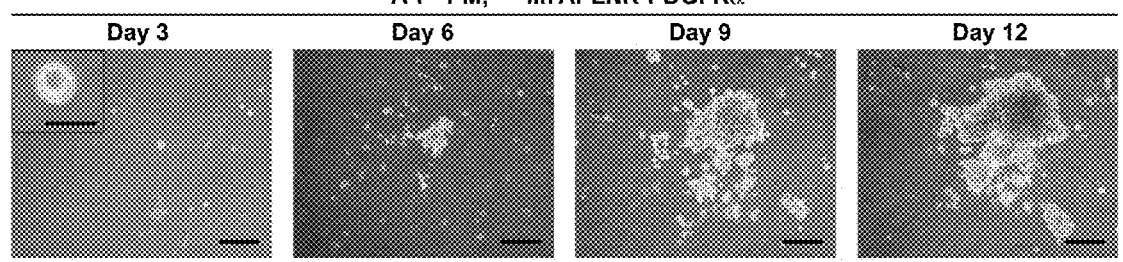
V+235+41- AHP; VE-cadherin+CD73-CD43lowCD235a+CD41a-
Day 3     Day 6     Day 9     Day 12
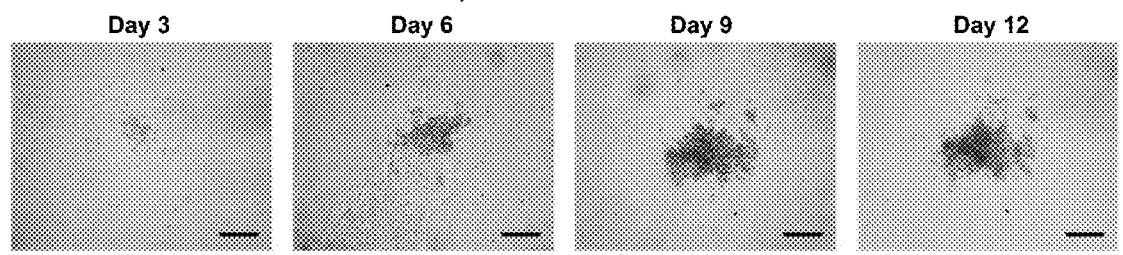
Fig. 12B
hESC/OP9 Coculture day 2.5
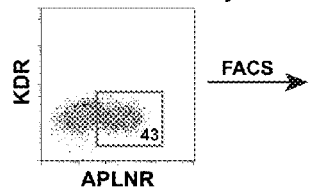 → FACS → APLNR+ subset Isolation → Coculture on OP9 → 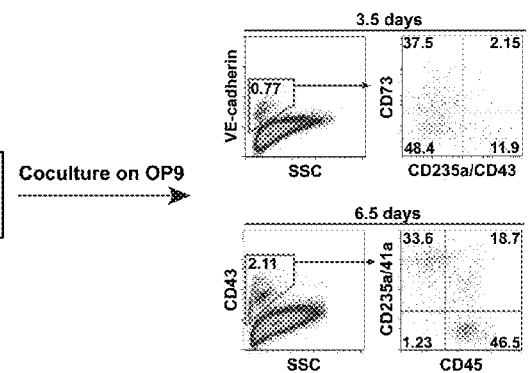

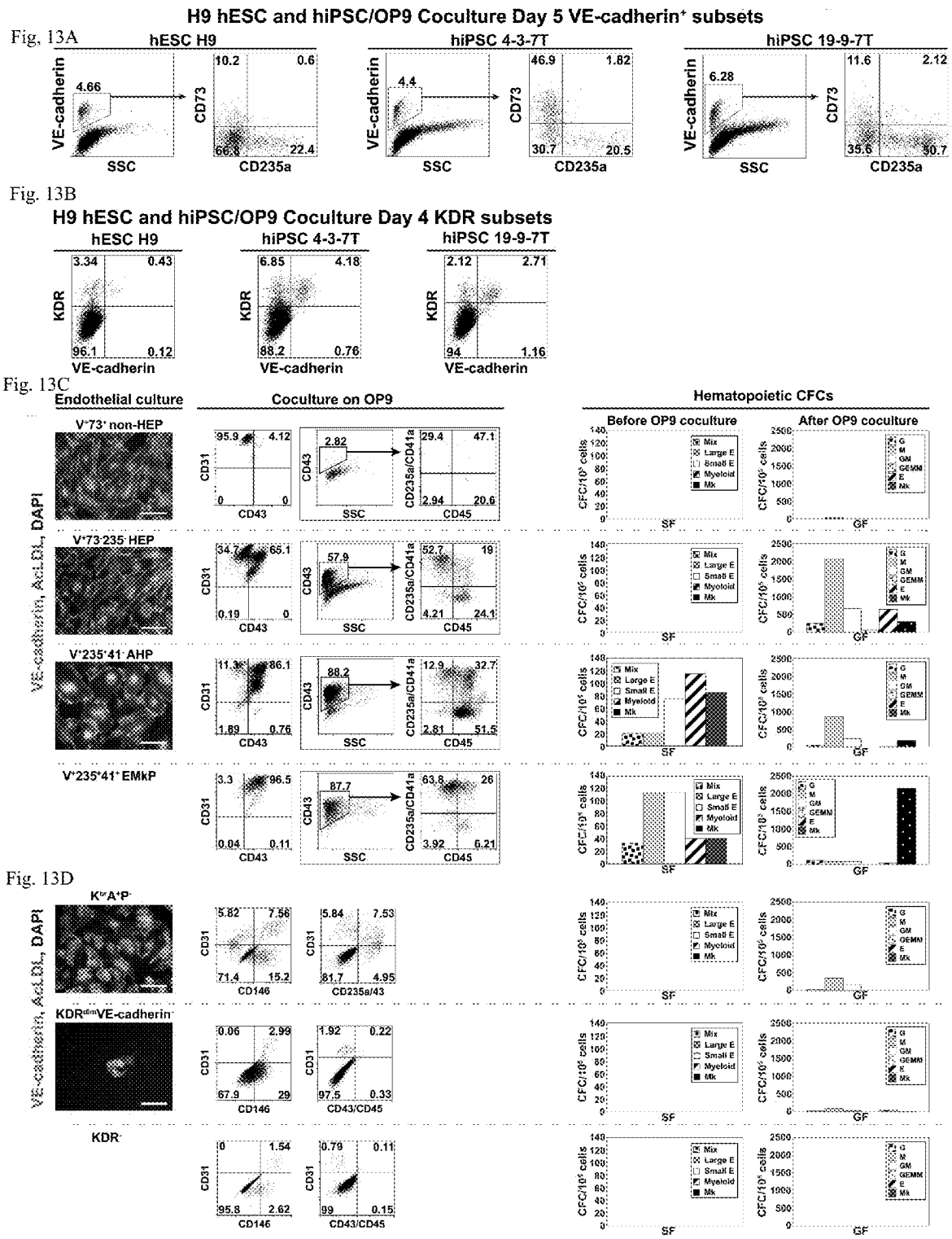

Fig. 16
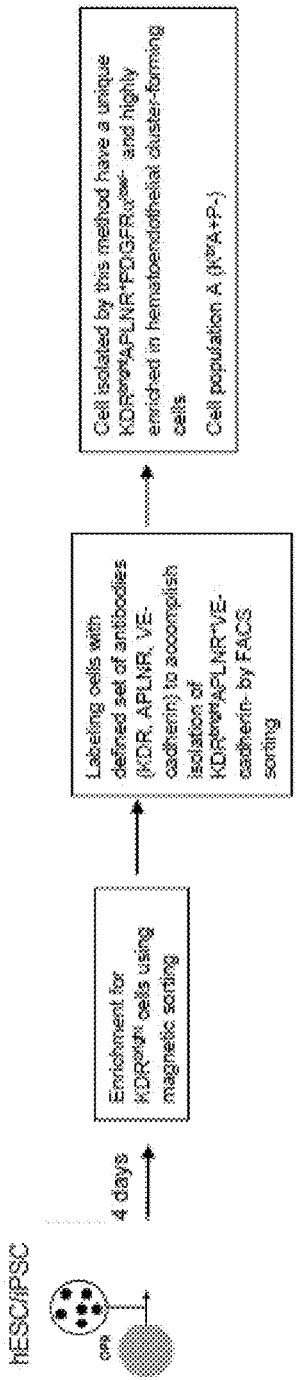
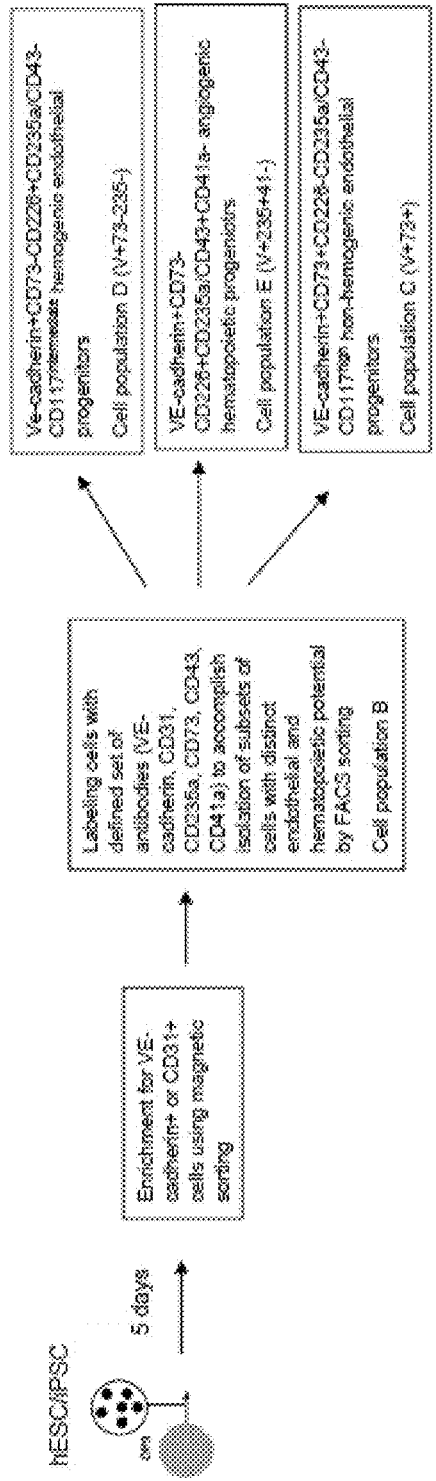

SEQUENCE LISTING

```
<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: PCR Primer

<400> SEQUENCE: 1
ccgacatcgc gacagcgaag c                                              21

<210> SEQ ID NO 2
<211> LENGTH: 24
<212> TYPE: DNA
<213> ORGANISM: Artificial Sequence
<220> FEATURE:
<223> OTHER INFORMATION: PCR Primer

<400> SEQUENCE: 2
gccatttcca gtccttccgt tttt                                           24

<210> SEQ ID NO 3
<211> LENGTH: 19
<212> TYPE: DNA
<213> ORGANISM: Artificial Sequence
<220> FEATURE:
<223> OTHER INFORMATION: PCR Primer

<400> SEQUENCE: 3
gccaagggcg agtcccgta                                                 19
```

```
<210> SEQ ID NO 4
<211> LENGTH: 27
<212> TYPE: DNA
<213> ORGANISM: Artificial Sequence
<220> FEATURE:
<223> OTHER INFORMATION: PCR Primer

<400> SEQUENCE: 4
gcatcttgct caactcggcg ttgtgca                                        27

<210> SEQ ID NO 5
<211> LENGTH: 23
<212> TYPE: DNA
<213> ORGANISM: Artificial Sequence
<220> FEATURE:
<223> OTHER INFORMATION: PCR Primer

<400> SEQUENCE: 5
caccagccca ggttaatccc cag                                            23

<210> SEQ ID NO 6
<211> LENGTH: 23
<212> TYPE: DNA
<213> ORGANISM: Artificial Sequence
<220> FEATURE:
<223> OTHER INFORMATION: PCR Primer

<400> SEQUENCE: 6
acccctgatt ctggtgtgga gga                                            23

<210> SEQ ID NO 7
<211> LENGTH: 21
<212> TYPE: DNA
<213> ORGANISM: Artificial Sequence
<220> FEATURE:
<223> OTHER INFORMATION: PCR Primer

<400> SEQUENCE: 7
acggtccgaa acgttggtct g                                              21

<210> SEQ ID NO 8
<211> LENGTH: 22
<212> TYPE: DNA
<213> ORGANISM: Artificial Sequence
<220> FEATURE:
<223> OTHER INFORMATION: PCR Primer

<400> SEQUENCE: 8
ccccagtctc ttgtgtgcct gg                                             22

<210> SEQ ID NO 9
<211> LENGTH: 21
<212> TYPE: DNA
<213> ORGANISM: Artificial Sequence
<220> FEATURE:
<223> OTHER INFORMATION: PCR Primer

<400> SEQUENCE: 9
cttgagcgag gctgcggttt c                                              21

<210> SEQ ID NO 10
<211> LENGTH: 21
<212> TYPE: DNA
<213> ORGANISM: Artificial Sequence
<220> FEATURE:
<223> OTHER INFORMATION: PCR Primer
```

<400> SEQUENCE: 10
ccagacgaac gctagagggc g                                    21

<210> SEQ ID NO 11
<211> LENGTH: 20
<212> TYPE: DNA
<213> ORGANISM: Artificial Sequence
<220> FEATURE:
<223> OTHER INFORMATION: PCR Primer

<400> SEQUENCE: 11
acgacgcgca caccaaggag                                      20

<210> SEQ ID NO 12
<211> LENGTH: 21
<212> TYPE: DNA
<213> ORGANISM: Artificial Sequence
<220> FEATURE:
<223> OTHER INFORMATION: PCR Primer

<400> SEQUENCE: 12
agctggcctt ccaaatgccg t                                    21

<210> SEQ ID NO 13
<211> LENGTH: 24
<212> TYPE: DNA
<213> ORGANISM: Artificial Sequence
<220> FEATURE:
<223> OTHER INFORMATION: PCR Primer

<400> SEQUENCE: 13
ggtggcatgc agatacattg gata                                 24

<210> SEQ ID NO 14
<211> LENGTH: 24
<212> TYPE: DNA
<213> ORGANISM: Artificial Sequence
<220> FEATURE:
<223> OTHER INFORMATION: PCR Primer

<400> SEQUENCE: 14
tccagagaaa cacatttccc actc                                 24

<210> SEQ ID NO 15
<211> LENGTH: 23
<212> TYPE: DNA
<213> ORGANISM: Artificial Sequence
<220> FEATURE:
<223> OTHER INFORMATION: PCR Primer

<400> SEQUENCE: 15
tgcaggagga agacacagca ccc                                  23

<210> SEQ ID NO 16
<211> LENGTH: 24
<212> TYPE: DNA
<213> ORGANISM: Artificial Sequence
<220> FEATURE:
<223> OTHER INFORMATION: PCR Primer

<400> SEQUENCE: 16
aacgtgcatt ctgagggctg tcat                                 24

<210> SEQ ID NO 17

```
<211> LENGTH: 23
<212> TYPE: DNA
<213> ORGANISM: Artificial Sequence
<220> FEATURE:
<223> OTHER INFORMATION: PCR Primer

<400> SEQUENCE: 17
cctggaggag aagaggaaag aga                                           23

<210> SEQ ID NO 18
<211> LENGTH: 25
<212> TYPE: DNA
<213> ORGANISM: Artificial Sequence
<220> FEATURE:
<223> OTHER INFORMATION: PCR Primer

<400> SEQUENCE: 18
ttgaggacct ctgtgtattt gtcaa                                         25
```

ANGIOHEMATOPOIETIC PROGENITOR CELLS

CROSS-REFERENCE TO RELATED APPLICATIONS

This application is a continuation application of U.S. patent application Ser. No. 13/590,591, filed Aug. 21, 2012, which claims priority to U.S. Provisional Application Ser. No. 61/526,520, filed Aug. 23, 2011, which is incorporated herein by reference in its entirety.

STATEMENT REGARDING FEDERALLY SPONSORED RESEARCH OR DEVELOPMENT

This invention was made with government support under HL081962 and HL099773 awarded by the National Institutes of Health. The government has certain rights in the invention.

BACKGROUND

Establishing a system for de novo generation of hematopoietic stem cells (HSCs) from human pluripotent stem cells (hPSCs) would open a unique opportunity to study human HSC development and provide a novel source of therapeutic cells for blood disease. Achieving this goal requires a detailed understanding of cellular and molecular pathways that lead to blood formation from hPSCs and identification of the immediate precursors of multipotential hematopoietic cells.

Avian, mouse and human embryonic studies demonstrated that definitive HSCs which give rise to all lineages of an adult hematopoietic system are generated in the aorta-gonad-mesonephros (AGM) region and are located at the ventral aspect of the dorsal aorta (de Bruijn et al., 2002; Ivanovs et al., 2011; Pardanaud et al., 1996; Taoudi and Medvinsky, 2007). In this area, hematopoietic cells arise from a unique population of endothelial cells known as hemogenic endothelium (HE) through an endothelial-hematopoietic transition (EHT) (Boisset et al., 2010; Jaffredo et al., 2000; Zovein et al., 2008). Dynamic tracing and imaging studies conducted in vivo demonstrated that EHT represents a continuous process in which cells with endothelial characteristics gradually acquire hematopoietic morphology and phenotype (Bertrand et al., 2010; Boisset et al., 2010; Kissa and Herbomel, 2010).

Definitive hematopoiesis in the AGM region is preceded by primitive hematopoiesis in the yolk sac, which initially generates primitive erythrocytes, megakaryocytes, and macrophages (Palis et al., 1999; Xu et al., 2001). The second wave of yolk sac hematopoiesis, defined as erythromyeloid hematopoiesis, is associated with expansion of erythroid precursors producing adult β hemoglobin and unilineage and multilineage myeloid precursors (Palis et al., 1999). Although the concept of HE was coined based on observations of blood formation within the aorta, it is also known that endothelium lining nascent capillaries in the yolk sac (Ferkowicz et al., 2003) and possibly vitelline and umbilical arteries (Yokomizo and Dzierzak, 2010) have the capacity to generate blood as well.

The demonstrations of HSC formation from endothelium emphasized the need for access to well-defined populations of HE cells in hPSC cultures in order to develop technologies for de novo generation of HSCs from human induced pluripotent (hiPSCs) or embryonic stem cells (hESCs). In the embryo definitive HE can be identified based on anatomical location, morphology, and expression of Runx1 (Jaffredo et al., 2010; North et al., 1999; North et al., 2002). Because these criteria cannot be entirely applied to cells differentiated in vitro, the precise identification of HE in hPSC cultures remained as a significant challenge. Although VE-cadherin$^+$CD41a$^-$ and/or CD45$^-$ phenotype is commonly used for detection and isolation of HE, it has very limited utility in human PSC cultures since it covers the entire population of endothelial cells, does not fully exclude hematopoietic cells, and does not discriminate between endothelial lineages with restricted primitive hematopoietic and multipotential definitive potentials. In addition, the direct mesodermal precursor of HE with definitive hematopoietic potential remains largely unknown.

Needed in the art is an improved method of generating HE progenitors and generating novel populations of hemogenic endothelial cells, angiogenic blood cells or endothelial progenitors.

BRIEF SUMMARY OF THE INVENTION

In one embodiment, the present invention is a purified human cell population of hematovascular mesodermal precursors (Cell Population A), wherein the population is at least 94% pure and wherein the cells are characterized as VE-cadherin$^-$, KDR$^{bright}$, APLNR$^+$, PDGFRα$^{low}$. In one embodiment, the cells are capable of forming hematoendothelial colonies with at least 1 in 10 frequency.

In another embodiment, the present invention is a purified human cell population of hemogenic endothelial progenitors (Cell Population D, VE-cadherin+,CD73−CD235a/CD43−); angiogenic hematopoietic progenitors (Cell Population E, VE-cadherin+CD235a/CD43+CD41a−) or non-hemogenic endothelial progenitors (Cell Population C, VE-cadherin+ CD73+), wherein the cell population is at least 94% pure.

In another embodiment, the hemogenic endothelial cells are CD117$^{intermediate}$.

In another embodiment, the angiogenic hematopoietic progenitor cells are CD73−.

In another embodiment, the non-hemogenic endothelial progenitors cells are CD117$^{high}$ and CD73+.

In another embodiment, the present invention is a method of examining a drug for ability to modify cell differentiation, comprising the step of exposing at lease one of the cell populations described above to a test drug and observing the effect of the drug on cell growth, differentiation or viability.

In another embodiment, the present invention is a method of obtaining the cell populations above comprising the steps of culturing pluripotent stem cells so that hematoendothelial differentiation occurs, and sorting the cells by cell markers selected from the group consisting of KDR, APLNR, VE-cadherin, PDGFRα, CD31, CD235a, CD73, CD43 and CD41a such that a purified cell population of the cells is obtained.

In an embodiment, the present invention is a method of treating a patient, comprising the step of supplying the at least one of the cell populations above in a therapy selected from the group of bone marrow transplantation, blood transfusion, immunotherapy, treatment of cardiovascular diseases, treatment of ischemia, diabetic ulcers, regeneration of vasculature, and artificial tissue constructs.

In an embodiment, the present invention is the method of treating a patient in need of blood cell reconstitution and/or restoration of endothelial cell activity comprising the step of administering the cell population above to a patient, wherein the cells will differentiate into blood cells or endothelial cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 12A is a characterization of hematopoietic and endothelial potential of day 3 A$^+$P$^+$ PM cells which show after culture in serum-free clonogenic medium A$^+$P$^+$ cells form FGF2-dependent colonies composed of hematopoietic blast cells (BL or HB-CFCs). The formation of these colonies proceeds through endothelial intermediate (core) stage. Insert in the upper left panel show HB cores at high magnification; bar=50 μm. Although V$^+$235$^+$41$^-$ AHPs require FGF2 for colony formation as well, they do not form endothelial core in clonogenic medium. Bars=200 μm.

FIG. 12B is a characterization of hematopoietic and endothelial potential of day 3 A$^+$P$^+$ PM cells and hematopoietic and endothelial potential of A$^+$P$^+$ cells after coculture with OP9 for 3.5 and 6.5 days.

FIG. 13A is a generation and characterization of angiohematopoietic progenitors from hiPSCs and H9 hESCs an identification of day 5 VE-cadherin$^+$.

FIG. 13B is a generation and characterization of angiohematopoietic progenitors from hiPSCs and H9 hESCs, day 4 mesodermal cell subsets in differentiated H9 hESCs and hiPSCs cultures.

FIG. 13C is a generation and characterization of angiohematopoietic progenitors from hiPSCs and H9 hESCs which show functional characterization of day 5 VE-cadherin subsets obtained from hiPSC 19-9-7T.

FIG. 13D is a generation and characterization of angiohematopoietic progenitors from hiPSCs and H9 hESCs which show functional characterization of day 4 mesodermal subsets obtained from hiPSC 19-9-7T. Immunofluorescent images show endothelial cultures of corresponding subsets stained with VE-cadherin and AcLDL; bars=100 µm. Dot plots show flow cytometric analyses of corresponding iPSC-derived subsets after coculture on OP9. Hematopoietic CFC potential evaluated in serum-containing METHOCULT (GF) and in serum-free METHOCULT (SF) supplemented with FGF2, SCF, IL6, IL3, and EPO.

FIG. 16 (top panel) shows a flowchart overview a method for generating angioblastic cells from human pluripotent stem cells; and (bottom panel) a method for generating subsets of embryonic endothelial cells with and without blood forming potential, and angiogenic blood cells.

DESCRIPTION OF THE INVENTION

Special note: We have altered the naming of two important bio-markers between the provisional application 61/526,520 and the present application. This is an alteration in naming convention only. "CD144" is now referred to as "VE-cadherin". "CD140a" is now referred to as "PDGFRα".

In General

It had been demonstrated that hematopoietic cells, including stem cells (HSCs), emerge from a specific subset of endothelial cells with a capacity to generate blood, hemogenic endothelial cells (HE), also referred to above and below as hemogenic endothelial progenitors (HEP), through endothelial-hematopoietic transition. However, the identity of the HE cells has remained obscure and specific features that distinguish HE from non-HE and discrete stages of endothelial transition into hematopoietic cells remains unknown.

In the present invention, using a human embryonic stem cell (hESCs) differentiation system, we have identified HE cells as a transient population of VE-cadherin$^+$CD235a/CD43−CD73− angiogenic cells with primary endothelial characteristics. These cells lack hematopoietic colony-forming potential but have the capability to generate hematopoietic cells after culture on stromal cells.

Although the HE cells shared many phenotypic features with emerging hematopoietic and non-HE cells including CD31, VE-cadherin, and CD117 expression, the cells could be reliably separated from non-HE cells and early hematopoietic cells with angiogenic potential based on CD73 and CD235a/CD43 expression, respectively. We could also distinguish HE cells from their predecessors, including $^{EHM}$lin−APLNR$^+$PDGFRα$^+$ mesodermal cells with the potential to form hemangioblast colonies, i.e. blast colony forming cells (BL-CFC), and $^{EHM}$lin−APLNR$^+$KDR$^{bright}$PDGFRα$^{low/−}$ angioblastic cells which form hematoendothelial colonies with 1 in 10 frequency but are also capable to differentiate into mesenchymal cells. (See FIG. 15 and the Examples for a further definition of $^{EHM}$lin− and lin−).

In one embodiment, the present invention also provides a human pluripotent stem cell-based platform (including hESCs and hiPSCs) for exploration of mechanisms guiding endothelial-hematopoietic transition and for identification of factors required for acquisition of hematopoietic stem cell potential by blood cells following transition from endothelium. hPSCs are human pluripotent stem cells which include embryonic stem cells and induced pluripotent stem cells. We have shown that hiPSCs behave in the same manner as hESCs.

Cell Populations of the Present Invention

Figure 15:
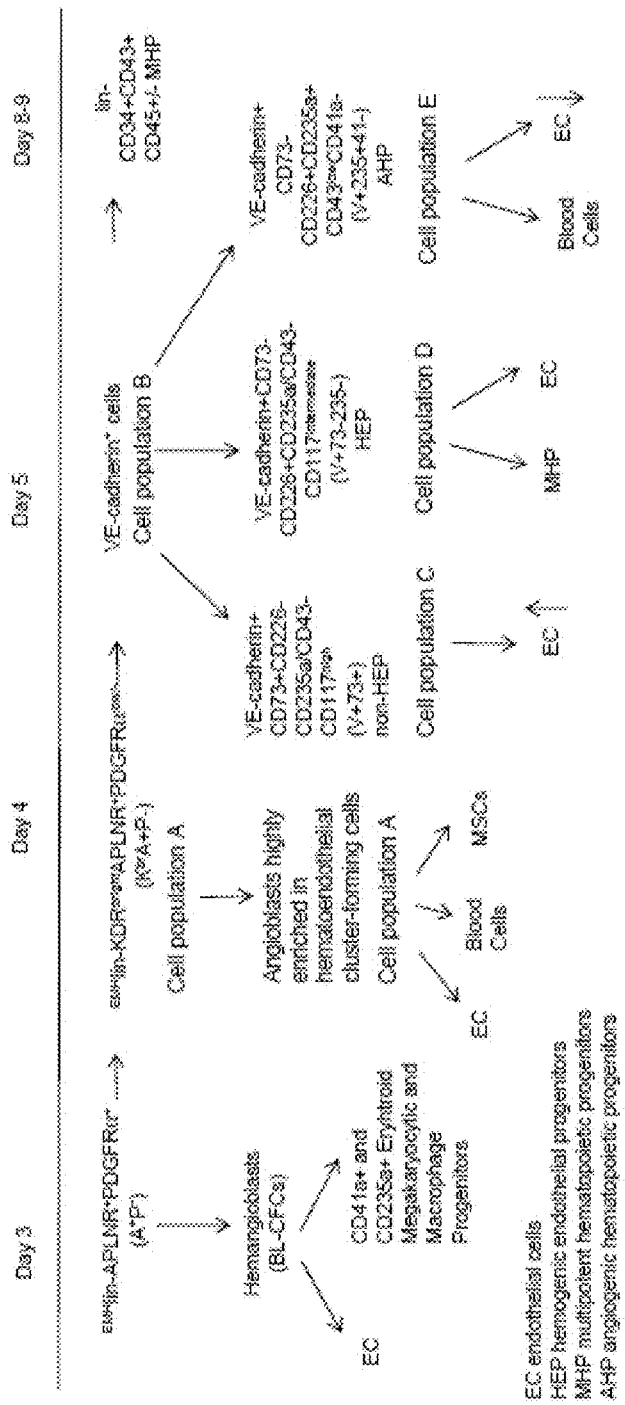
FIG. 15 shows a flowchart overview of a method for generating angiohematopoietic progenitors from human pluripotent stem cells.

In one embodiment, the present invention is a purified cell population of cells designated in FIG. 15 or 16 as Cell Population A, B, C, D or E. In specific embodiments, the cell populations are at least 94%, 95%, 98%, or 99% pure. The preferred minimum marker set is as follows:

Population A: VE-cadherin$^−$APLNR$^+$KDR$^{bright}$PDGFRα$^{low/−}$,

Population B: total VE-cadherin+ cells,

Population C: VE-cadherin+CD73+,

Population D: VE-cadherin+CD73−CD235a/43−, and

Population E: VE-cadherin+CD235a/43+CD41a−.

In general, one would begin the purification of the cell populations of the present invention by obtaining hESCs (human embryonic stem cells) or other pluripotent cell populations. The Examples disclose the use of hESC lines H1 and H9, which were obtained from WiCell Research Institute in Madison, Wis. One may also use induced pluripotent stem cells (iPSCs). We also disclose hiPSCs 4-3-7T and 19-9-7T (FIG. 13) in the Examples.

The hESC/iPSC lines are maintained in an undifferentiated state, preferably via one of many methods available for culture of hESCs in defined conditions. By "chemically defined conditions for human iPSC derivation and culture" we mean cultures without serum and other animal-derived components and conditions appropriate for production of clinical grade ESCs (e.g. Chen et al. Nat Methods. 2011 May; 8(5):424-9).

The pluripotent stem cells are then cultured under conditions that favor differentiation into a hematopoietic lineage. There are several techniques which can induce human pluripotent stem cells to differentiate into the hematopoietic lineage. In the Examples below, we use coculture with stromal cells, a previously described technique to induce hematopoietic differentiation as taught, for example, in U.S. Pat. No. 6,280,718, the disclosure of which is hereby incorporated by reference. One may also wish to induce human pluripotent stem cells to differentiate into the hematopoietic lineage by embryonic body method or 2D cultures. It is believed that any other methodology for the generation of hematopoietic progenitors from pluripotent stem cells will follow a similar pattern and proceed through CD34+CD43+CD45− and CD34+CD43+CD45+ stages of multipotency.

In one embodiment, one would coculture the pluripotent stem cells with stromal cells such as OP9 to induce hematopoietic differentiation. "Hematoendothelial cells" is a broad term used to define populations of cells with hematopoietic and endothelial potential (e.g., Cell Populations A through E). Population D is hemogenic endothelium, which is defined in [0003]. Optionally, human cells can be depleted of OP9 using anti-mouse CD29 antibodies. We use a very dense overgrown OP9 monolayer to achieve successful hematopoietic differentiation in the Examples.

Figure 8:
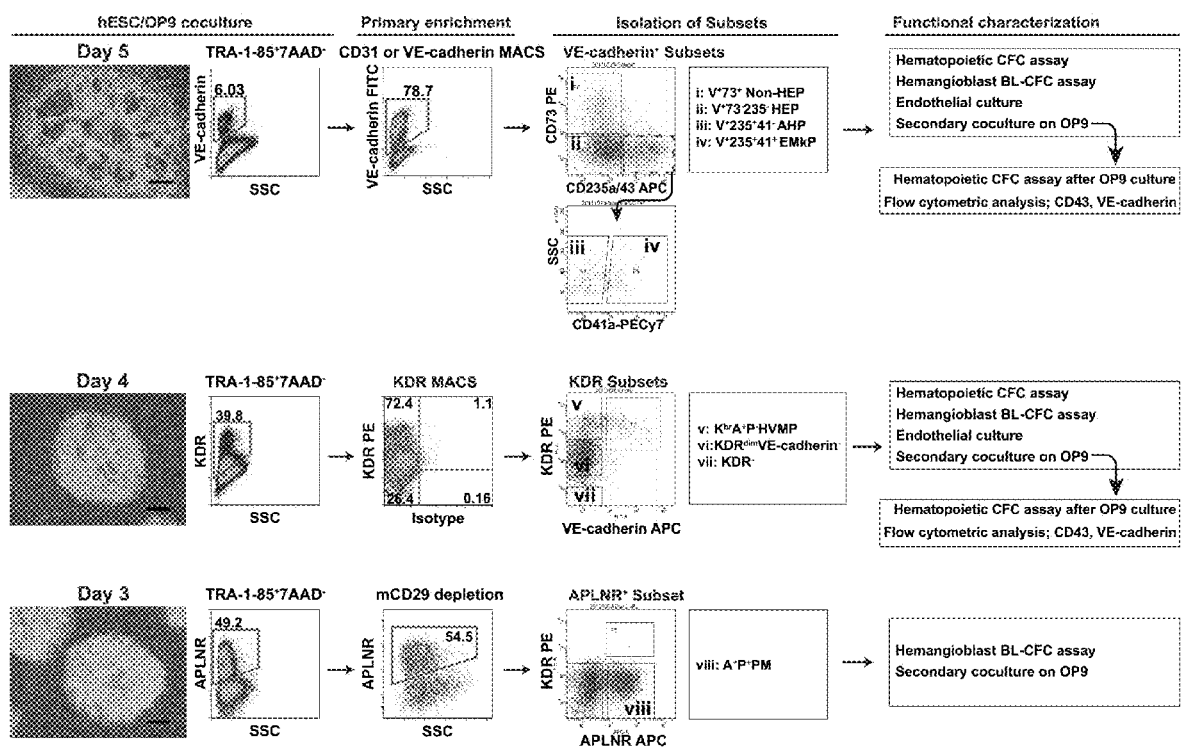
FIG. 8 is a schematic diagram of experimental procedure used for hESC/iPSC differentiation and isolation and analysis of cell subsets with hematopoietic and endothelial potential.

FIG. 8 describes a general approach for isolation of distinct cell populations. In one embodiment, one would isolate Cell Population A by coculturing for four days and then enriching for KDR bright cells using magnetic sorting. One would then isolate APLNR$^+$KDR$^{bright}$ VE-cadherin$^-$ by FACS sorting. The resulting cell population is described in, FIG. 15 and FIG. 16, below, and is highly enriched in hematoendothelial cluster forming cells.

We did not use PDGFRα for direct sorting, but we know that these cells are mostly negative for PDGFRα or express very low level of PDGFRα (FIG. 8A, upper row last histogram). Although we did not use this marker for sorting, the lack of PDGFRα or very low levels of PDGFRα is important for discrimination of Population A (angioblast cells) from more primitive $^{EHM}$lin−APLNR+PDGFRα+ mesodermal cells expressing primitive streak genes and genes associated with lateral plate and extraembryonic mesoderm. One does not have to use PDGFRα and APLNR antibodies for cell sorting in the present invention because we know that KDR$^{bright}$ cells are APLNR+PDGFRα$^{low/−}$. However if one uses a different differentiation system (for example, a system that generates KDR$^{bright}$ cells some of which are PDGFRα+ and/or APLNR−), these antibodies can be added to separate the desired cell population.

The Examples also disclose a typical preparation of additional cell populations with hematoendothelial potential of the present invention. For example, one would coculture the pluripotent stem cells and OP9 cells described above for a period of 5 days and sort cells as disclosed in FIG. 16. And FIG. 15. The resulting cell populations, most preferably at least 95% pure, are capable of diverse developmental fates, as disclosed in FIG. 15 and FIG. 16. Typical cell purity after one round of FACS sorting is at least 95%. However, one may wish to do a second round FACS sorting to achieve at least 99% of purity.

As FIG. 15 indicates, Cell Population C has an increased potential to become endothelial cells, Cell Population D has an increased potential to become hematopoietic progenitors or endothelial cells, and Cell Population E has a reduced potential to become endothelial cells and an increased potential to become hematopoietic progenitors. Cell Population A has the potential to become endothelial cells, hemogenic endothelium, and hematopoietic progenitors.

One may wish to use Cell Populations A-E for various commercial and therapeutic purposes, including those listed below.

Methods of the Present Invention

In one embodiment, the present invention provides a direct source of cells for production of hematopoietic stem cells and multipotent hematopoietic progenitors for bone marrow transplantation, blood transfusion, and immunotherapy. Populations A, D, and E would be the most appropriate to use in this embodiment. Potentially both of these populations can be transplanted to achieve bone marrow reconstitution. Alternatively, both of them can be used to obtain hematopoietic stem cell (HSCs) for transplantation through applying mechanical force or expression of genes required for acquisition of self-renewal potential.

In another embodiment, the present invention provides cells useful for direct administration for simultaneous blood cell reconstitution and restoration of endothelial cell activity. Preferably, Populations A, D, and E will be used for this embodiment. The administration will typically be achieved through intravenous or intra-bone-marrow injection.

In another embodiment, the present invention provides cell populations useful for treatment of cardiovascular diseases, including ischemic heart disease, atherosclerosis, and diabetic angiopathy. Typically, Populations A, C, D, and E will be used for this embodiment. These cells or endothelial cells grown in vitro from these cells can injected intravenously or directly into affected heart/organ or arteries feeding the affected heart/organ.

In another embodiment, the present invention provides cell populations useful for treatment of critical leg ischemia and diabetic ulcers. Typically, Populations A, C and D will be particularly useful for this embodiment. These cells, or endothelial cells generated from these populations, can be injected intravenously or into arteries supplying affected leg or soft tissue around a diabetic ulcer. In addition, these cells can be used to make cellular patches for healing.

In another embodiment, the present invention provides cell populations useful for regeneration of vasculature following trauma and/or burn injury. Preferably Populations A, C, and D are useful for this embodiment. These cells, or endothelial cells generated from these populations, can be injected intravenously around a burn ulcer, or can be used to make cellular patches for healing and promoting of vascularization of burned areas.

In another embodiment, the present invention provides cell populations useful for incorporation into artificial tissue constructs to achieve tissue vascularization. Preferably, Populations A, C, and D will be useful for this embodiment. These cells can be added to a tissue construct. Alternatively, a digital tissue printing device can be used to deposit cells and promote vasculature formation within organs. Another potential use for these populations is applying the populations for construction of artificial blood vessels.

In another embodiment, the cell populations of the present invention are used in drug testing. One may wish to know whether a specific test agent has an impact on differentiation of any of the cell populations of the present invention. For example, one may wish to evaluate testing of small-molecules and drugs regulating endothelial-hematopoietic transition and formation of hematopoietic stem cells (HSC) from endothelium.

The following is a sample testing protocol: $^{EHM}$lin$^-$APLNR$^+$KDR$^{bright}$PDGFRα$^{low/−}$ (Cell Population A) or VE-cadherin$^+$CD235a/CD43$^-$CD73$^-$ (Cell Population D) will be cultured in conditions supporting hematoendothelial development in the presence/absence of a drug. The formation of specific cell types, such as endothelial and blood cells from progenitors, will be evaluated by flow cytometry for presence of markers, such as CD43+ hematopoietic and VE-cadherin+CD43− endothelial cells. In addition, formation of hematoendothelial clusters may be evaluated using immunofluorescence by double-staining with CD43 and VE-cadherin antibodies. Time-lapse recording of cell cultures could be performed to observe endothelial-hematopoietic transition in culture.

The drug effect on hematoendothelial transition may be evaluated based on the ratio of the blood/endothelial cells generated from the culture.

To test a drug's effect on HSC formation, hematopoietic cells generated from $^{EHM}$lin$^-$APLNR$^+$KDR$^{bright}$PDGFRα$^{low/−}$ (Cell Population A) or VE-cadherin$^+$CD235a/CD43$^-$CD73$^-$ (Cell Population D) cells in the presence/absence of drug may be injected into irradiated NOD/SCID/IL2Rg−/− mice to evaluate long term bone marrow repopulation potential.

In another embodiment of the present invention, one may wish to determine the optimal mechanical (shear stress)

force required for augmentation of hematopoietic potential of endothelial cells and acquisition of hematopoietic reconstitution potential by hematopoietic cells formed from the endothelium through endothelial-hematopoietic transition.

$^{EHM}$lin⁻APLNR⁺KDR$^{bright}$PDGFRα$^{low/-}$ (Cell Population A) that uniquely express TRPA1 mechanoreceptor or VE-cadherin⁺CD235a/CD43⁻CD73⁺/⁻ cells (Cell Population D and C) will be cultured under static conditions or pulsatile shear stress. TRPA1 is expressed by neurons, but we found that TRPA1 is also expressed in Cell Population A. This result indicates that this population can respond to mechanical stimuli in a different way, i.e. through the TRPA1 receptor. Potentially, this mechanoreceptor can be important for modulation of endothelial-hematopoietic transition and HSC development. We do not see significant TRPA1 expression in any other cell populations we identified in OP9 coculture. This is why we refer to TRPA1 as a unique marker and we consider it to be a very important marker.

The formation of endothelial and blood cells from progenitors will be evaluated by flow cytometry for presence CD43+ hematopoietic and VE-cadherin+CD43− endothelial cells. In addition, formation of hematoendothelial clusters will be evaluated using immunofluorescence by double-staining with CD43 and VE-cadherin antibodies. Time-lapse recording of cell cultures could be performed to observe endothelial-hematopoietic transition in culture. The shear stress effect on hematoendothelial transition will be evaluated based on ratio of the generated blood/endothelial cells. To test a shear stress effect on HSC formation, hematopoietic cells generated from $^{EHM}$lin⁻APLNR⁺KDR$^{bright}$PDGFRα$^{low/-}$ (Cell Population A) or VE-cadherin⁺CD235a/CD43⁻CD73⁻ cells (Cell Population D) in the presence/absence of shear stress may be injected into irradiated NOD/SCID/IL2Rg−/− mice to evaluate long term bone marrow repopulation potential.

In another embodiment, the present invention provides cell populations useful for testing drugs that specifically target blood cancer cells at the level of hematoendothelial progenitors. For these purposes, one would typically use iPSCs generated from blood cancer cells (for example iPSCs derived from chronic myeloid leukemia cells; Hu et al, Blood 2011, 117(14):e109-119). Blood cancer-derived iPSCs will be obtained to generate bipotential hematoendothelial progenitors: $^{EHM}$lin⁻APLNR⁺KDR$^{bright}$PDGFRα$^{low/-}$ (Cell Population A), VE-cadherin⁺CD235a/CD43⁻73⁻ (Cell Population D) or VE-cadherin⁺CD235a/CD43⁺ (Cell Population E) cells. These cells will be used to find drugs that selectively affect viability, expansion, and differentiation potential of distinct types of hematoendothelial progenitors.

For example, chronic myeloid leukemia (CML) cells have chromosomal damage in only endothelial and blood cells. This damage indicates that a chromosomal brake is happening at the level of bipotential hematoendothelial progenitors. Therefore, to eradicate CML we need to find drugs that affect hematoendothelial progenitors. Currently, lineage-restricted hematopoietic progenitors are used for drug screening. These drugs may not affect hematoendothelial progenitors and, therefore, CML cannot be cured at present time.

In another embodiment of the present invention, one may wish to test drugs affecting angiogenic blood cells and non-angiogenic progenitors. Although angiogenic inhibitors show promise for cancer treatment in mouse models, the inhibitors show limited effect in clinical trials. This may be because the drugs have a different effect on different types of endothelial progenitors.

$^{EHM}$lin⁻APLNR⁺KDR$^{bright}$PDGFRα$^{low/-}$ (Cell Population A), VE-cadherin⁺CD235a/CD43⁻CD73− (Cell Population D) or VE-cadherin⁺CD235a/CD43⁺CD41a⁻ (Cell Population E) cells can be used to assay a drug effect on proliferation, migration and tube formation by endothelial cells derived from these progenitors. In addition, MATRIGEL™ sponge, tumor growth assays, and in vivo imaging can be used to assay the effect of a drug on angiogenic potential of described subsets.

EXAMPLES

Introduction

In the examples below, we show that HE progenitors (HEPs) can be generated from hPSCs and be identified precisely based on VE-cadherin (CD144) expression but the lack of CD73 and CD235a/CD43 expression. We demonstrate that HEPs represent a transient population of cells with the stroma-dependent capacity to generate the entire spectrum of myeloid progenitors including 0-hemoglobin producing erythroid cells and pan-myeloid CFC-GEMM. In addition, we found that the earliest VE-cadherin⁺CD73⁻CD43$^{low}$CD235a⁺CD41a⁻ blood cells retain endothelial potential and possess a unique FGF2-dependent hematopoietic colony-forming activity. A novel population of endothelial progenitors lacking hematopoietic potential (non-HEPs) was distinctively recognized by the expression of CD73 and a high level of CD117, i.e. VE-cadherin⁺CD73⁺CD235a/CD43⁻CD117$^{high}$ phenotype. VE-cadherin⁺CD73⁻CD43/CD235a⁻ HE cells originated from $^{EMH}$lin−KDR$^{bright}$APLNR⁺PDGFRα$^{low/-}$ hematovascular mesodermal precursors (HVMP), which were highly enriched in cells forming hematoendothelial clusters on OP9 stromal cells. These progenitors were distinct from the more primitive $^{EMH}$lin−APLNR⁺PDGFRα⁺ mesoderm that contained a population of hemangioblasts (HBs), which have the capacity to form colonies composed of primitive type blood cells through endothelial intermediates in serum-free semisolid medium.

Results

Identification of Functionally Distinct Progenitors with Hematopoietic and/or Endothelial Potential within Emerging Embryonic VE-Cadherin⁺ Cells Based on Expression of CD73 and CD235a.

To characterize the development of various mesodermal lineages, we employed the hPSC differentiation system in coculture with OP9 (Choi et al., 2009a; Vodyanik et al., 2006; Vodyanik et al., 2010). In these cultures, we have previously identified CD43 as a marker for hPSC-derived progenitors that have the potential to form hematopoietic cytokine-dependent colonies in semisolid medium and demonstrated that CD43 expression separates hematopoietic cells from endothelial cells (Choi et al., 2009a; Vodyanik et al., 2006). To investigate the developmental steps immediately preceding the formation of CD43⁺ blood cells and map the diverging point of hematopoietic and endothelial cell lineages, we analyzed the kinetic expression of various endothelial markers following H1 hESC differentiation in OP9 coculture.

Figure 1A:
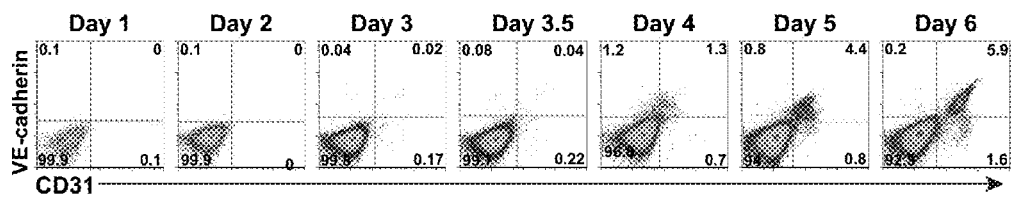
FIG. 1A is a characterization of major subsets of VE-cadherin$^+$ cells generated from hESCs after 5 days of coculture on OP9, which shows the kinetics of VE-cadherin and CD31 expression in differentiated H1 hESCs.
Figure 7A:
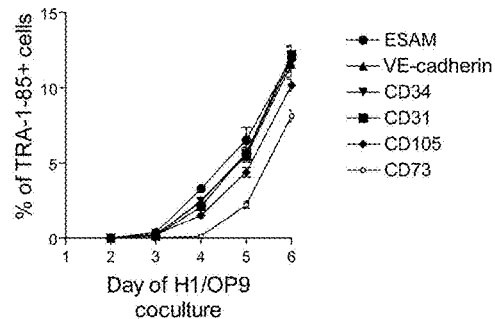
FIG. 7A is a characterization of day 5 VE-cadherin+ subsets in hESC/OP9 coculture and an expression of typical endothelial markers in differentiated H1 hESCs in OP9 coculture as determined by flow cytometry at days 1 through 6 of differentiation. The percentages of positive cells were determined within the population of viable human cells (7AAD$^-$TRA-1-85$^+$). Error bars are means±SE of 3 independent experiments.

The first cells expressing VE-cadherin endothelial marker (Breier et al., 1996) were detected by day 4 of differentiation (FIGS. 1A and 7A). Upregulation of VE-cadherin expression on differentiated hESCs in OP9 coculture coincided with the expression of another endothelial marker CD31

Figure 7B:
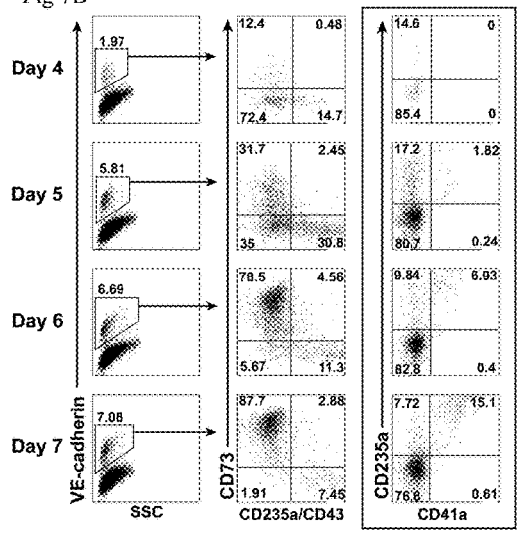
FIG. 7B is a characterization of day 5 VE-cadherin+ subsets in hESC/OP9 coculture and representative experiments to show kinetics of major VE-cadherin$^+$ subsets and expression of CD41a by CD235a cells in H1 hESC/OP9 coculture.

(PECAM) (FIG. 1A). Interestingly, cells expressing CD235a (Glycophorin A), a hematopoietic marker of erythroid lineage, could be detected within the first emerging VE-cadherin$^+$ cells (FIG. 7B). On the next day (day 5) of differentiation, the number of VE-cadherin$^+$ cells and the proportion of CD235a$^+$ cells within this population substantially increased. All of the VE-cadherin$^+$CD235a$^+$ cells were negative for CD41a (abbreviated as V$^+$235$^+$41$^-$ cells) on day 4 of differentiation.

Figure 1B:
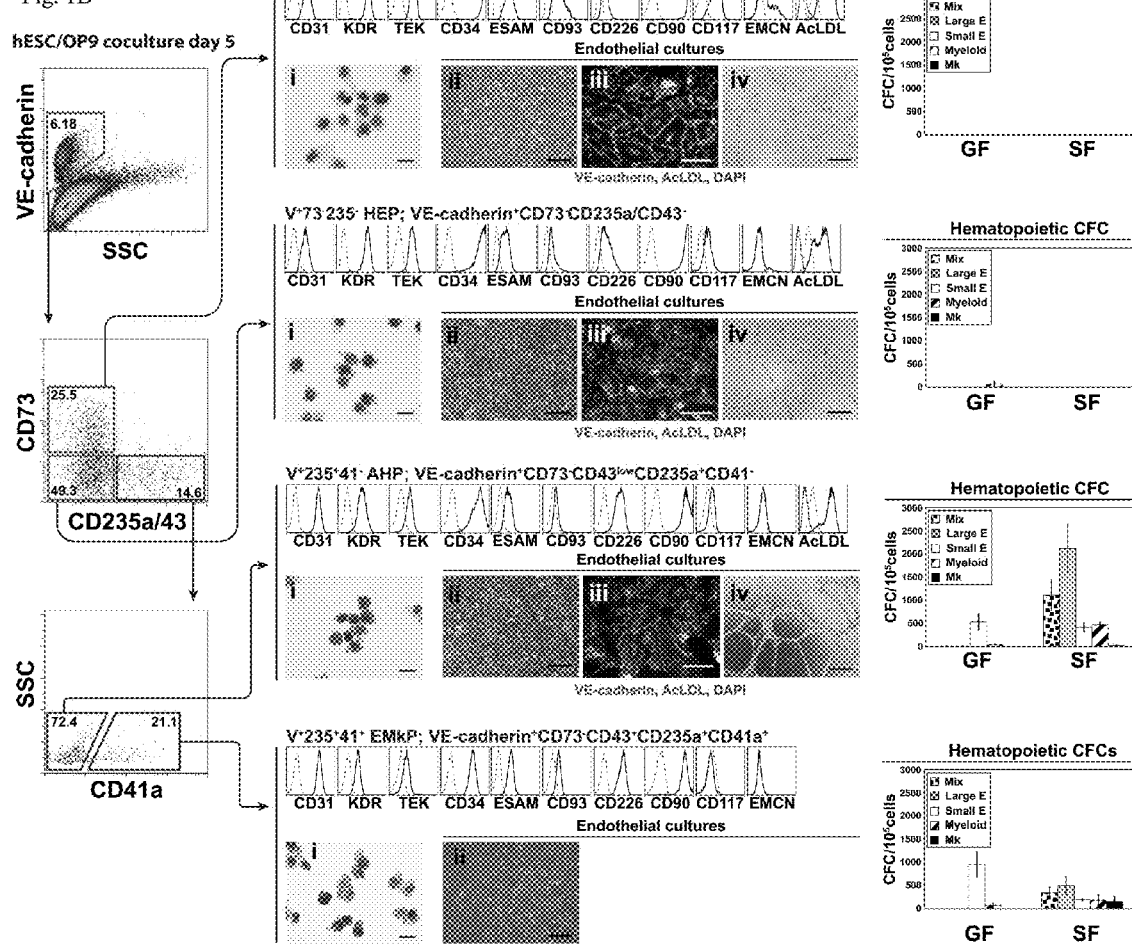
FIG. 1B is a characterization of major subsets of VE-cadherin$^+$ cells generated from hESCs after 5 days of coculture on OP9, which is a characterization of endothelial and hematopoietic CFC potentials of freshly isolated day 5 VE-cadherin$^+$ subsets. Histograms represent the expression of typical endothelial molecules by indicated cell subsets. AcLDL histograms show flow cytometric profiles of cells incubated with AcLDL at 37° C. (AcLDL uptake; black histogram) versus 4° C. (AcLDL binding control; gray histogram). (i) Wright-stained cytospins demonstrate morphology of isolated cells (bar=20 μm). Endothelial culture panels show (ii) phase contrast images (bar=400 μm), (iii) immunofluorescent analysis (bar=100 μm), and (iv) tube formation (bar=400 μm). Hematopoietic CFC potential of sorted day 5 VE-cadherin$^+$ subsets is evaluated in serum-free METHOCULT (SF) supplemented with FGF2, SCF, IL6, IL3, and EPO, and in standard serum-containing GF+ H4435 METHOCULT. Error bars are means±SE of three experiments.
Figure 7C:
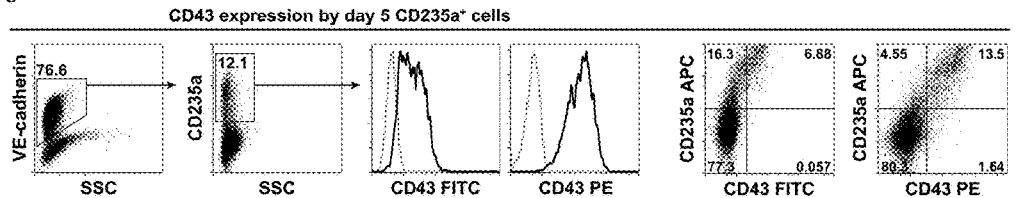
FIG. 7C is a characterization of day 5 VE-cadherin+ subsets in hESC/OP9 coculture and day 5 VE-cadherin$^+$ CD235a$^+$ weakly express CD43 which is best detected using PE-conjugated antibody. Flow analysis of VE-cadherin$^+$ cells selected by magnetic sorting is shown.

However, on day 5 of differentiation, a small proportion of CD235a$^+$ cells coexpressing CD41a (V$^+$235$^-$41$^+$ cells) could be detected (FIGS. 1B and 7B). Although V$^+$235$^+$41$^-$ cells expressed a high level of CD43 which defines hematopoietic commitment (Vodyanik et al., 2006), expression of CD43 in V$^+$235$^+$41$^-$ cells was relatively low and was best detectable with antibodies conjugated with APC or PE (FIG. 7C). Thus, we combined CD235a and CD43 antibodies in our studies to achieve optimal pan-hematopoietic detection at all stages of differentiation.

Figure 7D:
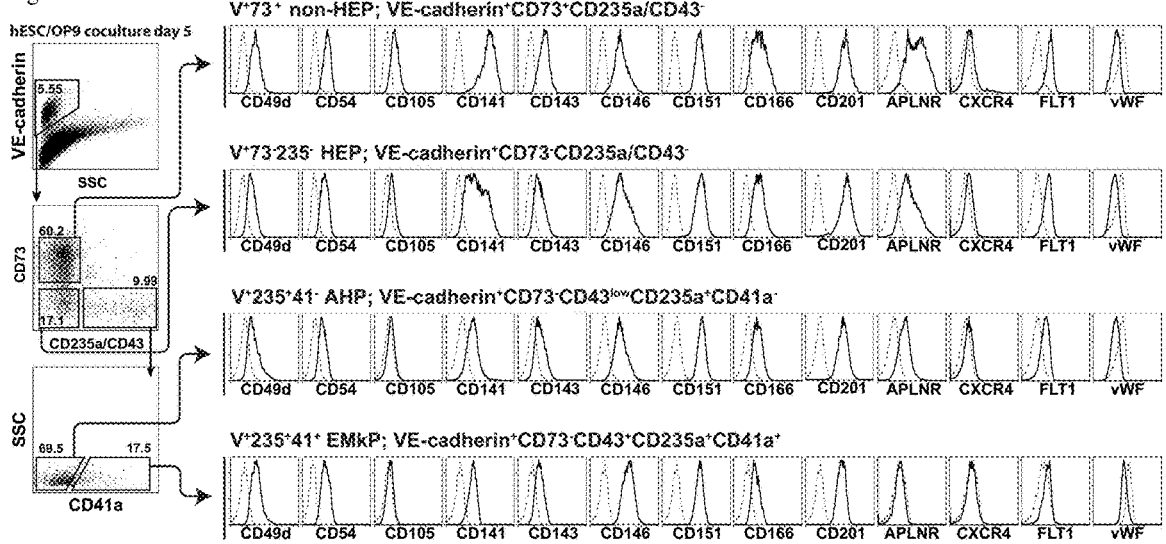
FIG. 7D is a characterization of day 5 VE-cadherin+ subsets in hESC/OP9 coculture and flow cytometric analysis of day 5 VE-cadherin$^+$ subsets.

Phenotypic analysis of day 5 VE-cadherin$^+$ cells revealed almost uniform expression of CD31, KDR, CD34, CD201, ESAM, and CD146 endothelial markers by these cells. However, we noticed that another typical endothelial marker, CD73 or 5'-nucleotidase (Thomson et al., 1990), was expressed only in 20-60% of total VE-cadherin$^+$ cells almost exclusively within the 235a/CD43$^-$ population (FIGS. 1B, 7B and 7D). This observation led us to identify three distinct major subsets within emerging VE-cadherin$^+$ cells: V$^+$235$^+$41$^-$, V$^+$73$^+$, and V$^+$73$^-$235$^-$ (FIG. 1B and Table 4). Kinetic analysis revealed that V$^+$73$^-$235$^-$ cells represent a transient population that develops during the earliest stages of endothelial commitment, but is mostly lost within the next 3 days of differentiation. The V$^+$73$^+$ population was minor at onset of endotheliogenesis, but gradually increased with advanced differentiation. The proportion of VE-cadherin$^+$ cells expressing 235a and/or CD43 hematopoietic markers peaked on day 5 of differentiation and then decreased (FIG. 7B).

As demonstrated in FIG. 1B, all three major VE-cadherin$^+$ cell subsets had very similar endothelial phenotype and were capable of acetylated low-density lipoprotein (AcLDL) uptake, indicative of endothelial function. However, we noticed that expression of CD117 (C-Kit), a marker for early stage angiohematopoietic progenitors, was highest in V$^+$73$^+$ cells, while its expression was almost undetectable in V$^+$235$^+$41$^-$ cells. V$^+$73$^-$235$^-$ cells expressed an intermediate level of CD117 (FIG. 1B). We also found that in contrast to other day 5 VE-cadherin$^+$ subsets, V$^+$73$^+$ cells lacked the expression of CD226 (DNAM-1), a cell surface marker typically found on the hematopoietic cells (Kojima et al., 2003; Shibuya et al., 1996). Morphologically, the V$^+$235$^+$41$^-$ population consisted predominantly of cells with a high nuclear-cytoplasmic ratio typical for immature hematopoietic cells (FIG. 1B).

In contrast, almost all V$^+$73$^+$ cells had characteristic endothelial morphology. V$^+$73$^-$235$^-$ cells had an intermediate morphology that resembled both V$^+$235$^+$41$^-$ and V$^+$73$^+$ cells, i.e. pale blue cytoplasm similar to endothelial cells, but higher nuclear-cytoplasmic ratio similar to immature hematopoietic cells.

To fully analyze the differentiation potential of each newly discovered VE-cadherin$^+$ cell subsets, they were isolated using FACS and cultured in endothelial conditions and assayed for hematopoietic colony-forming activity (FIG. 8). As shown in FIG. 1B, the three major day 5 VE-cadherin$^+$ subsets (V$^+$73$^-$235$^-$, V$^+$235$^+$41$^-$ and V$^+$73$^+$ cells), but not the minor V$^+$235$^+$CD41$^+$ subset, formed a monolayer of adherent cells with endothelial morphology when cultured on fibronectin in endothelial medium. Consistent with their endothelial nature, these cells expressed VE-cadherin, took up AcLDL, and formed vascular tubes in—MATRIGEL™ matrix.

Figure 9A:
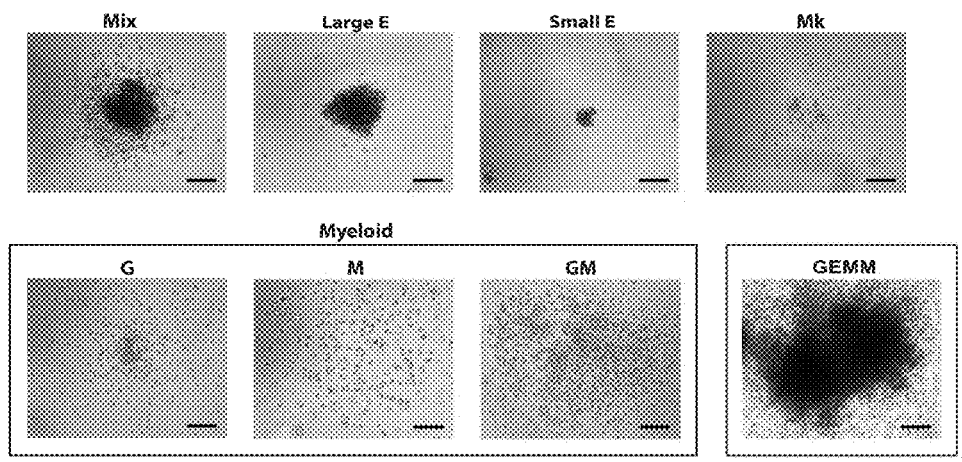
FIG. 9A is a characterization of hematopoietic CFC potential of day 5 V$^+$235$^+$41$^-$ AHPs and typical morphology of hematopoietic colonies formed by V$^+$235$^+$41$^-$ cells. GEMM colony formed from day 8 lin$^-$CD34$^+$CD43$^+$CD45$^+$CD38$^-$ cells in serum containing clonogenic medium is shown to emphasize a distinct morphological differences observed between classical GEMM colonies and Mix colonies formed from V$^-$235$^+$41$^-$ cells in serum free medium; bars=200 μm.
Figure 9B:
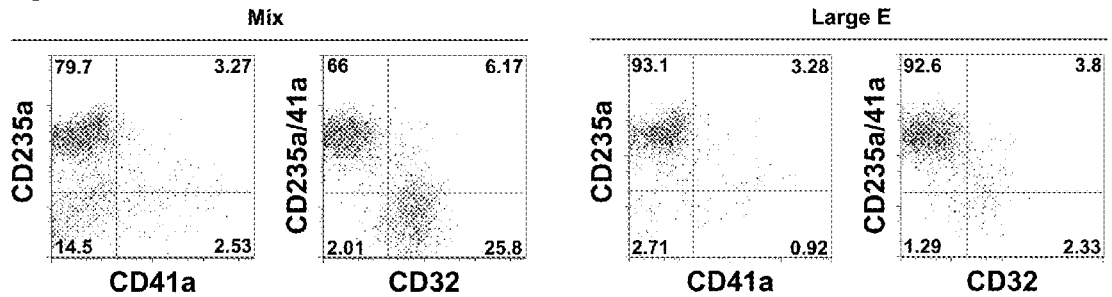
FIG. 9B is a characterization of hematopoietic CFC potential of day 5 V$^+$235$^+$41$^-$ AHPs and flow cytometric analysis demonstrated uniform expression of CD235a on cells forming large erythroid colonies. In contrast, mixed colonies are composed of CD235a$^+$ erythroid, CD41a$^+$ megakaryocytic and CD32$^+$CD235a/CD41a$^-$ myeloid cells.

In contrast, hematopoietic colony-forming (CFC) potential was detected almost exclusively within V$^+$235$^+$41$^-$ and V$^+$235$^+$41$^+$ cells. Although the hematopoietic CFC potential of V$^+$235$^+$41$^-$ cells in standard serum-based CFC medium was low and mostly restricted to small CFC-E, we found that the number and spectrum of hematopoietic CFCs was markedly increased in serum-free medium containing FGF2, SCF, EPO, IL-3, and IL-6. In the serum-free conditions, day 5 V$^+$235$^+$41$^-$ cells formed large erythroid, megakaryocyte, myeloid, and mixed colonies composed of erythroid cells, macrophages and megakaryocytes indicating that emerging blood cells expressing CD235a erythroid marker had multilineage potential (FIGS. 9A and 9B).

Figure 9C:
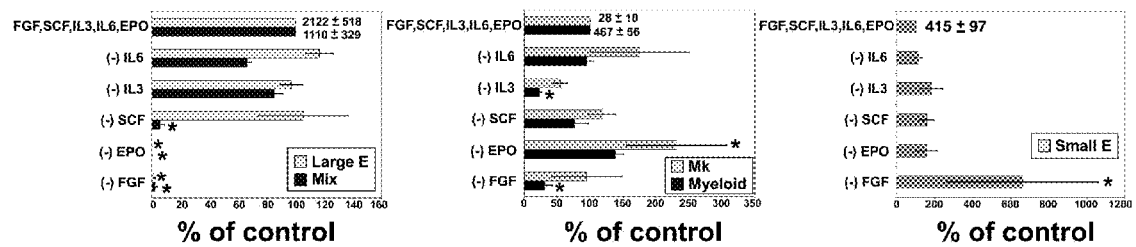
FIG. 9C is a characterization of hematopoietic CFC potential of day 5 V$^+$235$^+$41$^-$ AHPs and determination of optimal cytokine combination for the detection of hematopoietic CFC potential of V$^+$235$^+$41$^-$ cells in serum-free H4236 METHOCULT. The effect of removing individual cytokines from METHOCULT on the number of colonies is relative to control (100%, all cytokines added). The numbers above bars show control CFC counts (mean+SE) per 10$^5$ cells. Error bars represent standard error of 3 to 8 independent experiments. * p<0.01 as compared to control.

To define which growth factors are required for V$^+$235$^+$41$^-$ cells to form hematopoietic colonies, we eliminated each cytokine individually from clonogenic cultures. These experiments demonstrated that both FGF2 and EPO were essential for the development of large CFC-E and CFC-Mix (FIG. 9C). The removal of SCF almost entirely abrogated CFC-Mix, but had little effect on large CFC-E. Myeloid colonies required IL-3 and FGF2 for optimal development. The day 5 V$^+$235$^+$41$^+$ cells formed predominately CFC-E and -Mix however, they downregulated the expression of APLNR and TEK and failed to grow into endothelial cells in endothelial conditions indicating that the acquisition of the CD41a expression was associated with the complete loss of endothelial potential (FIGS. 1B and 7D).

Figure 2A:
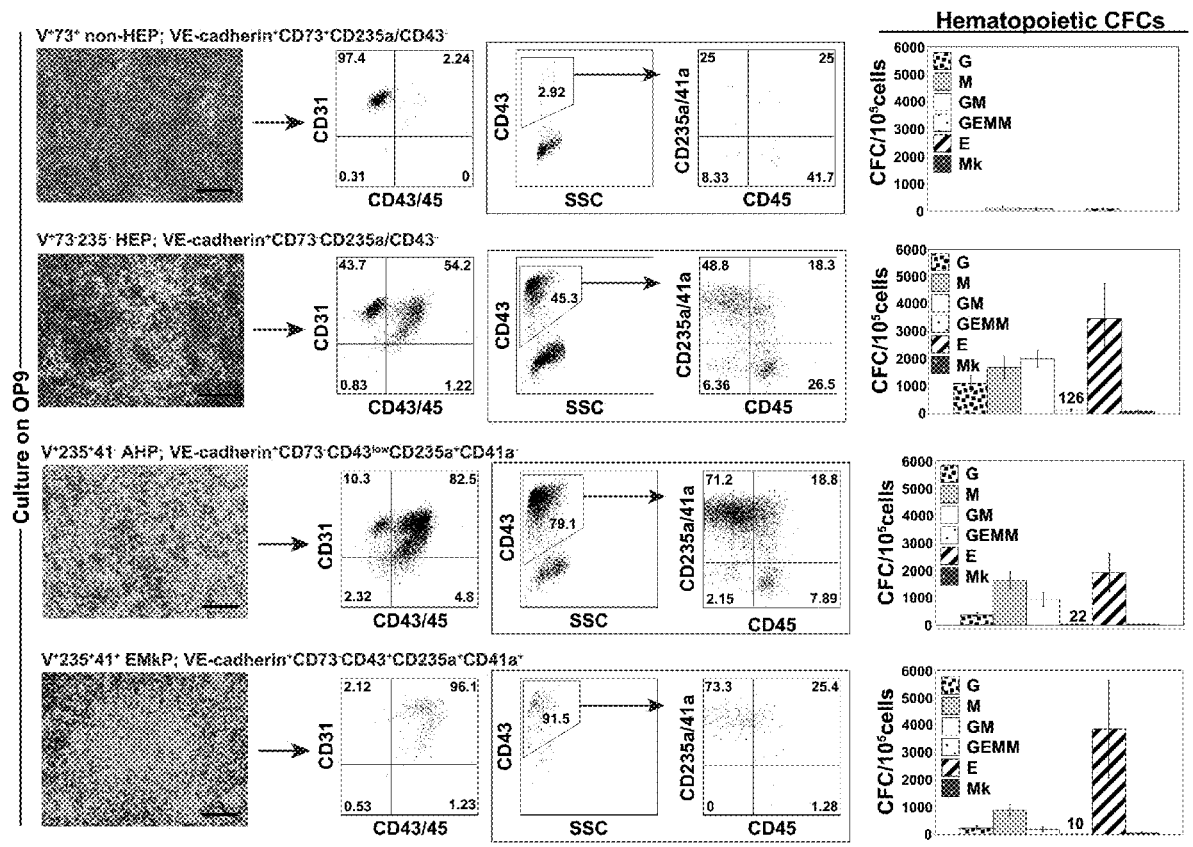
FIG. 2A demonstrates stroma-dependent hematopoietic and endothelial potential of day 5 VE-cadherin$^+$ subsets and shows a phase contrast images of cultures (bar=400 μm), flow cytometric analysis, and hematopoietic CFC potential (GF+ H4435 serum-containing METHOCULT) are shown. Error bars are means±SE of three experiments. The numbers show mean counts for CFC-GEMM.

Hemogenic potential of embryonic endothelial cells can be identified in culture with bone marrow stromal cells (Nishikawa et al., 1998; Oberlin et al., 2002), thus we cultured day 5 VE-cadherin$^+$ subsets on OP9 separately. In these conditions, both V$^+$73$^-$235$^-$ and V$^-$235$^+$41$^-$ cells generated CD31$^+$CD43/45$^-$ endothelial cells and a significant amount of CD43$^+$ blood cells (FIG. 2A). The CD43$^+$ cells consisted of CD235a/CD41a$^+$ erythromegakaryocytic cells and CD235a/CD41a$^-$CD45$^{-/-}$ multipotent hematopoietic progenitors (MHP) which we typically observe from hESCs differentiated on OP9 for 8-9 days (Vodyanik et al., 2006). These day 8-9 CD235a/CD41a$^-$CD45$^{-/-}$ MHP express CD34 but lack of CD38 and other hematopoietic lineage markers, i.e. they have a lin$^-$CD34$^+$CD43$^+$CD45$^{+/-}$CD38$^-$ phenotype (Vodyanik et al., 2006). Although both V$^+$73$^-$235$^-$ and V$^+$235$^+$41$^-$ cells generated a broad range of hematopoietic colonies in standard serum-containing CFC medium after culture on OP9, V$^+$73$^-$235$^-$ cells formed the higher numbers of myeloid colonies, including large multicentric pan-myeloid GEMM colonies. In contrast, V$^+$73$^+$ cells formed mostly endothelial cells with very few hematopoietic cells (FIG. 2A).

Figure 2B:
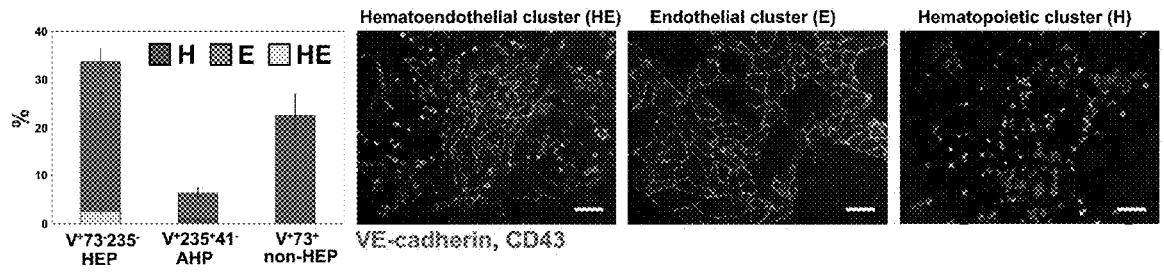
FIG. 2B demonstrates stroma-dependent hematopoietic and endothelial potential of day 5 VE-cadherin$^+$ subsets and is a single-cell deposition assay to detect the frequency of endothelial, hematopoietic, and bipotential hematoendothelial progenitors. Immunofluorescent staining of clusters formed by single cells after 10-12 days of culture on OP9 using CD43 and VE-cadherin antibodies is shown (bar=100 μm). Graph shows the frequency of each type of progenitor as a percentage of cluster-containing wells versus total cell-deposited wells. Error bars are means±SE of three experiments.

To determine the frequency of progenitors with hematopoietic and endothelial potential of each subset of day 5 VE-cadherin$^+$ subset, we performed a single cell deposition assay. As shown in FIG. 2B, V$^+$73$^+$ single cells generated only endothelial clusters on OP9 with a frequency of about ⅕, while V$^+$235$^+$41$^-$ cells formed predominantly hematopoietic cell clusters. Although the majority of V$^+$73$^-$235$^-$ cells gave rise to either hematopoietic or endothelial clusters, 2.5% of them had the potential to form hematoendothelial clusters, indicating the presence of bipotential progenitors within this population.

Based on the functional and phenotypical properties of each VE-cadherin$^+$ subset, we defined them as the following: 1) V$^+$73$^-$235$^-$ are HEPs that have primary endothelial characteristics lacking hematopoietic CFC potential and surface markers, but expressing an intermediate level of CD117 and are capable of generating blood and endothelial cells upon coculture with stromal cells; 2) V$^+$235$^+$41$^-$ are angiogenic hematopoietic progenitors (AHPs) that possess primary hematopoietic characteristics but are capable of generating endothelial cells; 3) V$^+$73$^+$ are non-HEPs that have all functional and molecular features of endothelial cells, form endothelial colonies on OP9, and express high level of early progenitor marker CD117 (see also Table 4).

Figure 3A:
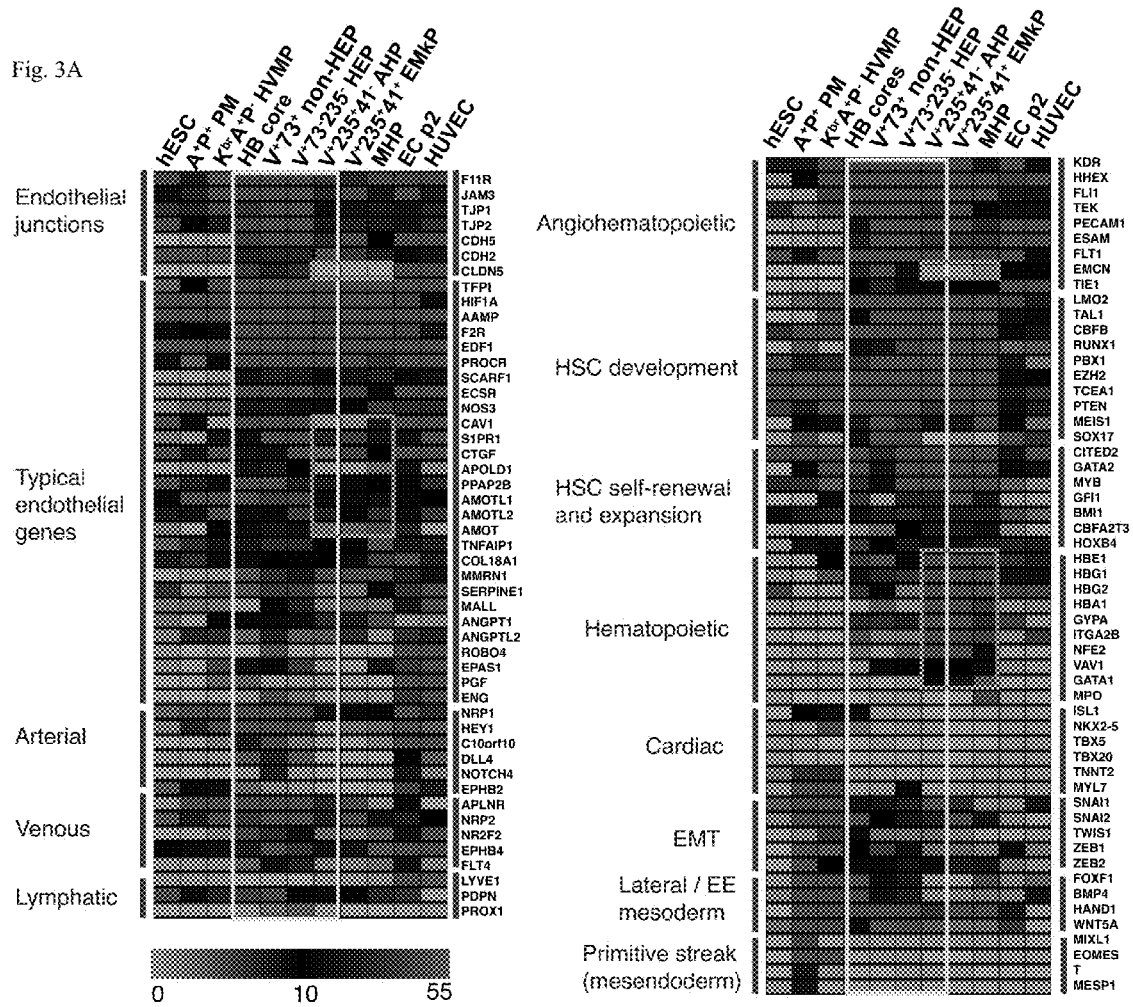
FIG. 3A is a gene expression profile of undifferentiated H1 hESCs, differentiated H1 hESC cell populations, and human umbilical endothelial cells and shows heat maps of selected genes associated with endothelial and hematopoietic cells, epithelial-mesenchymal transition (EMT), lateral plate/extraembryonic (EE) mesoderm, and primitive streak. HB core are endothelial intermediates formed by hemangioblasts in serum-free clonogenic medium. EC p2 are second passage of endothelial cells obtained from day 8 CD31$^+$CD43$^-$ differentiated H1 cells. HUVEC are human umbilical endothelial cells. See Table 4—for other abbreviations. The gene expression levels are estimated in terms of "transcripts per million".
Figure 3B:
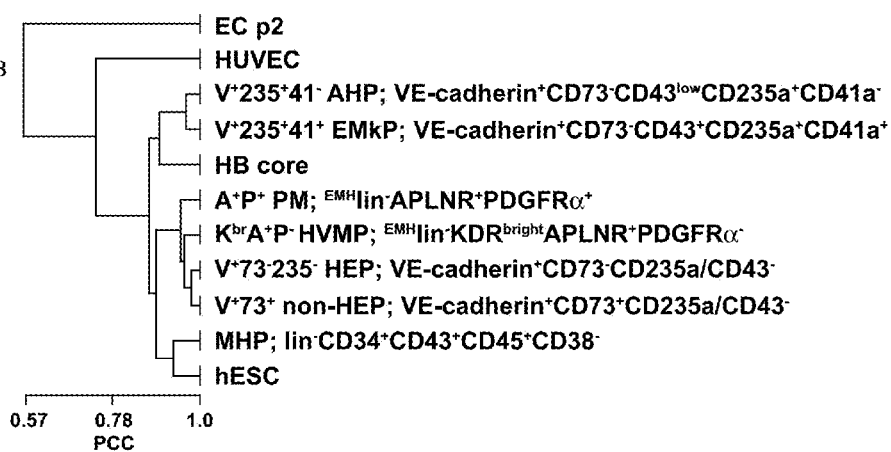
FIG. 3B is a gene expression profile of undifferentiated H1 hESCs, differentiated H1 hESC cell populations, and human umbilical endothelial cells which shows Pearson correlation analysis of global gene expression.
Figure 10A:
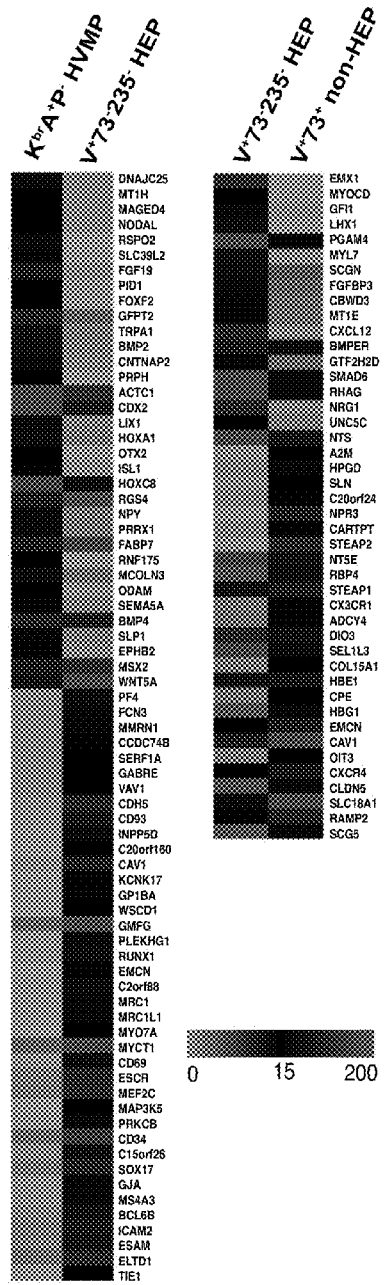
FIG. 10A is an analysis of differentially expressed genes in the day 5 VE-cadherin+ subsets and day 4 HVMPs where heat maps display the top overexpressed genes with at least five-fold differences in expression as estimated in tpm values.

Molecular profiling studies revealed a high similarity between the day 5 VE-cadherin$^+$ population subsets. All subpopulations of these cells expressed the typical endothelial genes, TFP, HIF1A, AAMP, F2R, EDF1, and PROCR, and the genes associated with angiohematopoietic and HSC development, FLI1, TEK, LMO2, TAL1, RUNX1, CBFB, PBX1, PTEN, and TCEA1. However, V$^+$235$^+$41$^-$ AHPs expressed higher levels of hematopoietic-specific genes and lower levels of the typical endothelial (CAV1, CTGF, APOLD1, and AMOT) and endothelial junction (CDH5, CDH2, and CLDN5) genes (FIG. 3A). In contrast, V$^+$73$^-$235$^-$ HEPs expressed higher levels of the endothelial genes, CLDN5, CAV1, and MMRN1N, and lacked the expression of hematopoietic genes. In comparison with the HEPs, the V$^+$73$^+$ non-HEPs expressed higher levels of the endothelial genes EMCN, CAV1, CXCR4, CLDN5, and COL15A1 (FIG. 10). Genes found to be more highly expressed in HEPs versus non-HEPs included NTS neurotensin BMPER an endothelial regulator that controls BMP4-dependent angiogenesis (Heinke et al., 2008) and SMAD6, a negative regulator of BMP signaling (Ishida et al., 2000) and RUNX1 activity (Knezevic et al., 2011).

Figure 4A:
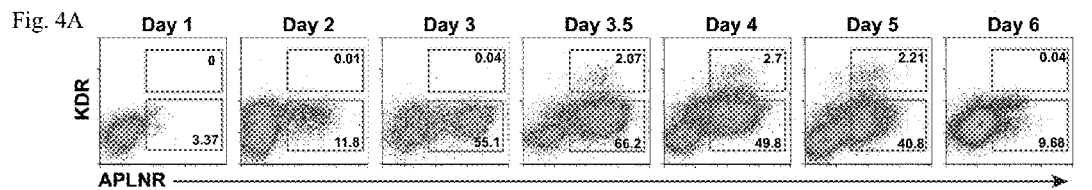
FIG. 4A demonstrates phenotypic and functional characterization of major subsets of day 4 hESC-derived mesodermal cells and shows kinetics of expression of APLNR and KDR in differentiated H1 hESCs.

Hemogenic Endothelial Cells Originate from a Unique $^{EMH}$lin–KDR$^{bright}$APLNR$^+$PDGFRα$^{low/-}$ Population of Mesodermal Cells with Hematovascular Potential To identify the direct mesodermal precursor of HE cells, we analyzed the expression of mesodermal markers APLNR (D'Aniello et al., 2009; Vodyanik et al., 2010), KDR (Shalaby et al., 1997), and PDGFRα (PDGFRα) (Kataoka et al., 1997) in differentiated hESCs before the first VE-cadherin$^+$ cells could be detected. This analysis revealed the population of KDR$^{bright}$APLNR$^+$ cells which was initially detected on day 3.5 of differentiation (FIG. 4A) immediately preceding the formation of the first VE-cadherin$^+$ cells in hESC/OP9 coculture (FIG. 1A).

Figure 4B:
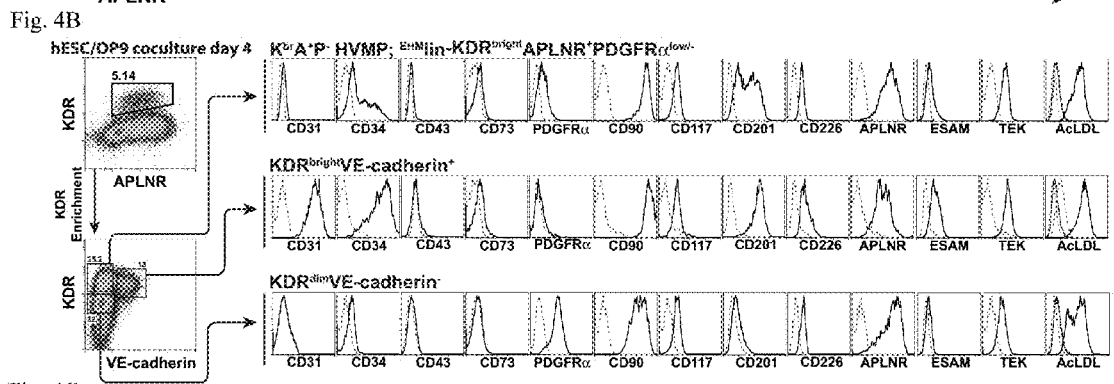
FIG. 4B demonstrates phenotypic and functional characterization of major subsets of day 4 hESC-derived mesodermal cells and shows the flow cytometric analysis of day 4 hESC-derived mesodermal cells that were first magnetically sorted for the KDR$^+$ population.

Emerging day 3.5 KDR$^{bright}$APLNR$^+$ cells essentially lacked the typical CD31, VE-cadherin endothelial, CD73, CD105 mesenchymal/endothelial, and CD43, CD45 hematopoietic cell markers (here on referred to as $^{EMH}$lin$^-$ cells) however, the early VE-cadherin$^+$ cells became clearly detectable within this population from day 4 of differentiation (FIG. 4B). Flow cytometric analysis of day 4 VE-cadherin$^-$KDR$^{bright}$APLNR$^+$ cells revealed that they maintain $^{EMH}$lin$^-$ phenotype ($^{EMH}$lin$^-$KDR$^{bright}$APLNR$^+$). However, in contrast to the more primitive day 2 and day 3 APLNR$^+$ (Vodyanik et al., 2010) and day 4 KDR$^{dim}$ mesodermal cells, day 4 $^{EMH}$lin$^-$KDR$^{bright}$APLNR$^+$ cells had downregulated expression of PDGFRα (FIG. 4B).

Figure 11A:
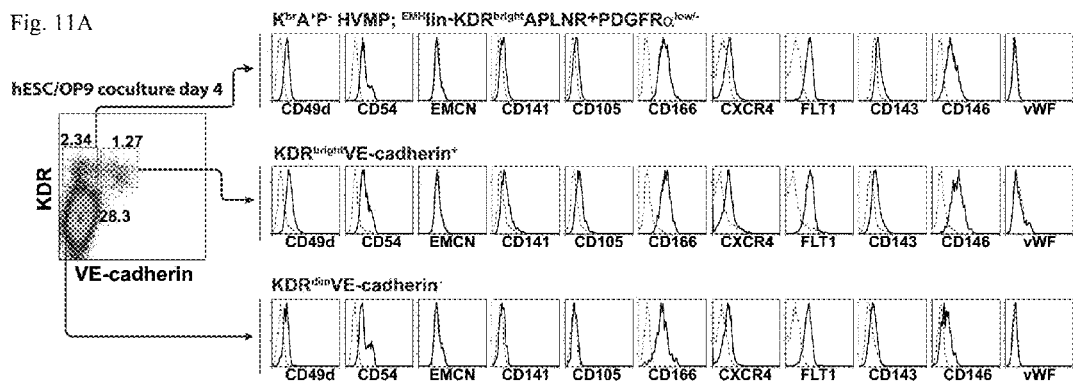
FIG. 11A is a characterization of day 3.5 and 4 mesodermal subsets and shows flow cytometric analysis of day 4 mesodermal subsets. Total population of human (TRA-1-85$^+$) cells analyzed.

Although these day 4 $^{EMH}$lin$^-$KDR$^{bright}$APLNR$^+$ PDGFRα$^{low/-}$ (K$^{br}$A$^+$P$^-$) cells lacked the most specific endothelial markers VE-cadherin and CD31, they expressed other markers typically found on endothelial cells including TEK, CD34, CD201, and CD146 (FIGS. 4B and 11A) suggesting that these mesodermal cells could be direct precursors of endothelial progenitors in hESC cultures. To confirm our hypothesis, we isolated day 4 K$^{br}$A$^+$P$^-$, KDR$^{dim}$, and KDR$^-$ cells using flow cytometry (FIG. 4C) and cultured them on OP9.

Figure 4C:
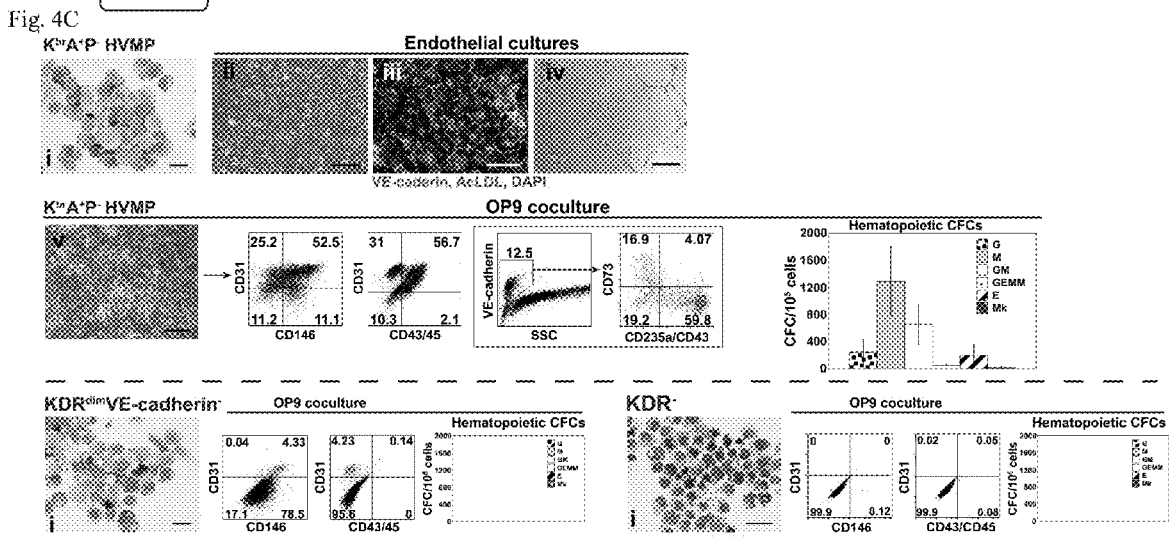
FIG. 4C demonstrates phenotypic and functional characterization of major subsets of day 4 hESC-derived mesodermal cells and shows endothelial and hematopoietic differentiation potential of indicated day 4 mesodermal subsets. (i) Wright-stained cytospins of freshly isolated cells (bar=20 μm). Endothelial culture panels show (ii) phase contrast images (bar=400 μm), (iii) immunofluorescent analysis (bar=100 μm), and (iv) tube formation (bar=400 μm) by K$^{br}$A$^+$P$^-$ cells. (v) shows phase contrast image of K$^{br}$A$^+$P$^-$ cell cultures on OP9. Flow cytometric analysis shows a developmental potential of KDR subsets after secondary OP9 coculture. Hematopoietic CFC potential of KDR subsets was evaluated after secondary coculture on OP9 using standard H4435 GF+ serum-containing METHOCULT. Error bars are means±SE of three experiments.
Figure 4D:
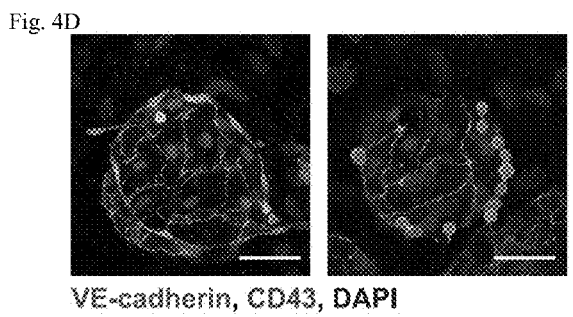
FIG. 4D demonstrates phenotypic and functional characterization of major subsets of day 4 hESC-derived mesodermal cells and illustrates confocal images of hematoendothelial clusters to demonstrate the early stages of endothelial-hematopoietic transition; bar=50 μm.
Figure 4E:
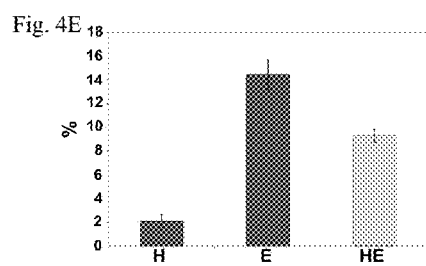
FIG. 4E demonstrates phenotypic and functional characterization of major subsets of day 4 hESC-derived mesodermal cells and shows a single-cell deposition assay to detect the frequency of endothelial (E), hematopoietic (H), and bipotential hematoendothelial (HE) progenitors within K$^{br}$A$^+$P$^-$ HVMPs. Graph shows the frequency of each type of progenitor as a percentage of cluster-containing wells versus total cell-deposited wells. Error bars are means±SE of three experiments.

As shown in FIG. 4C, after 5-6 days culture on OP9, only K$^{br}$A$^+$P$^-$ cells generated both CD31$^+$CD43/45$^-$ endothelial cells and CD43/CD45$^+$ hematopoietic cells, while KDR$^{dim}$ cells predominantly generated CD146$^+$CD31$^-$ mesenchymal cells, few endothelial cells, and almost no blood cells. KDR$^-$ cells lacked hematovascular potential completely. Importantly, day 4 K$^{br}$A$^+$P$^-$ cells generated V$^+$73$^-$235$^-$, V$^+$235$^+$41$^-$ and V$^+$73$^+$ subsets we observed on day 5 of primary hESC/OP9 coculture (FIG. 4C). It should be also noted that K$^{br}$A$^+$P$^-$ cells were multipotential and capable of differentiating into CD146$^+$CD31$^-$ mesenchymal cells in addition to blood and endothelial cells (FIG. 4C). Double staining of K$^{br}$A$^+$P$^-$ cells grown on OP9 with VE-cadherin and CD43 antibodies revealed that they form HE clusters, i.e. sheets of endothelial cells generating non-adherent blood cells (FIG. 4D). Morphological examination of HE clusters at different stages of development revealed that endothelial cells within these clusters gradually transitioned into hematopoietic cells. During the early stages of transition, VE-cadherin$^+$ cells had upregulated CD43 expression and transformed from a cuboidal to a round cell morphology (FIG. 4D). Single cell deposition experiments demonstrated that K$^{br}$A$^+$P$^-$ cells formed HE clusters at a high frequency (about 1 in 10 cells), strongly indicating that these cells represent the direct precursors of HE (FIG. 4E).

Figure 11B:
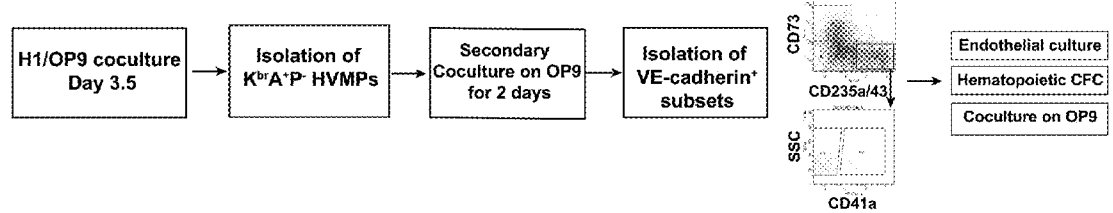
FIG. 11B is a characterization of day 3.5 and 4 mesodermal subsets and show a schematic diagram of experiments aimed to demonstrate the direct origin of HEPs and AHPs from HVMPs.
Figure 11C:
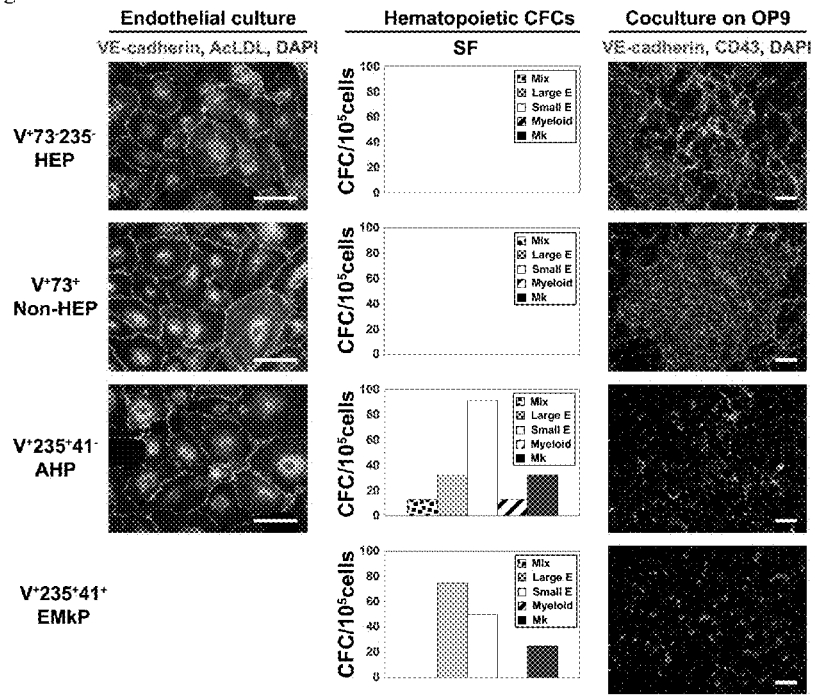
FIG. 11C is a characterization of day 3.5 and 4 mesodermal subsets and show endothelial and hematopoietic potential of indicated VE-Cadherin$^+$ subsets isolated from secondary culture of day 3.5 HVMPs on OP9 for 2 days (corresponds to day 5.5 of regular OP9 coculture). Hematopoietic CFC potential of freshly sorted VE-Cadherin$^+$ subsets derived from day 3.5 HVMPs was evaluated in serum-free METHOCULT (SF) supplemented with FGF2, SCF, IL6, IL3, and EPO. Bars are 100 μm.

To confirm that K$^{br}$A$^+$P$^-$ cells were direct precursors of the HEPs, we isolated these cells from day 3.5 of hESC/OP9 cocultures, before VE-cadherin$^+$ cells became detectable (see FIG. 1A), and recultured them on OP9 for 2 days. Flow cytometric analysis of these K$^{br}$A$^+$P$^-$ secondary cultures revealed that they had upregulated VE-cadherin expression and differentiated into V$^+$73$^-$235$^-$, V$^+$235$^+$41$^-$ and V$^+$73$^+$ subsets we observed on day 5 of primary hESC/OP9 coculture (FIG. 11B). When these subsets were isolated from the secondary cocultures by FACS and analyzed for endothelial and hematopoietic potentials, we found that the V$^+$73$^-$235$^-$, V$^+$235$^+$41$^-$ and V$^+$73$^+$ cells generated from isolated day 3.5 K$^{br}$A$^+$P$^-$ cells had the same hematopoietic and endothelial differentiation potentials as the primary day 5 HEP, AHP, and non-HEP subsets, respectively (FIG. 11C).

Morphologic analysis revealed that K$^{br}$A$^+$P$^-$ cells were large blast-like cells, noticeably different from KDR$^{dim}$ and KDR$^-$ cells which had a more abundant and vacuolated cytoplasm (FIG. 4C). Molecular profiling studies revealed that in K$^{br}$A$^+$P$^-$ cells, expression of transcriptional regulators of hematopoietic and endothelial development (LMO2, TAL1, CBFB, GATA2, and FLI1) was upregulated, while expression of the primitive streak genes (MIXL1, EOMES, T, and MESP1) was downregulated (FIG. 3A). However, these cells retained high expression levels of genes representing lateral plate/extraembryonic mesoderm (FOXF1, BMP4, and WNT5A). Based on their phenotypic features, gene expression profile, morphology, and functional properties we designated K$^{br}$A$^+$P$^-$ mesodermal cells as hematovascular mesodermal precursors, (HVMP). These precursors may resemble embryonic angioblasts which are defined as cells that have not yet formed a lumen and express certain (but not all) endothelial markers. They are committed to differentiate into endothelial cells and give rise to vascular primordia (Risau and Flamme, 1995).

Figure 14:
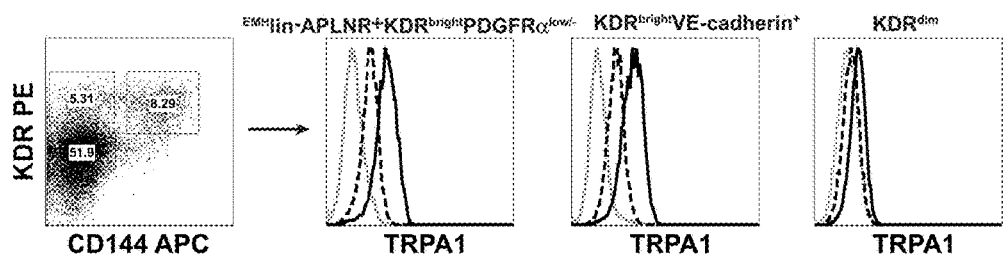
FIG. 14 is a set of histograms demonstrating flow cytometric analysis of TRPA1 expression by mesodermal cells. Histograms show TRPA1 staining with (dashed histogram) and without (black histogram) TRPA1 blocking peptide.

K$^{br}$A$^+$P$^+$ cells uniquely expressed TRPA1, a gene that encodes the subfamily A, member 1 protein of a transient receptor potential cation channel family. TRPA1 contains ankyrin repeats, and is believed to function as a mechanoand chemoreceptor (Corey et al., 2004; Macpherson et al., 2007). Using an antibody against the extracellular epitope of TRPA1, we confirmed that day 4 $^{EMH}$linKDR$^{bright}$APLNR+ PDGFR low/− and VE-cadherin+ cells expressed this molecule (FIG. 14).

BL-CFCs Represent Angiohematopoietic Progenitors with Primitive Hematopoietic Potential Originating from $^{EMH}$lin⁻APLNR⁺PDGFRα⁺ Mesoderm Blast CFCs (BL-CFCs) were identified by the Keller group as progenitors that generate blast colonies composed of cells with hematopoietic and endothelial potential (Choi et al., 1998). Widely referred to as hemangioblasts (HBs), BL-CFCs represent the earliest cells with detectable hematopoietic potential in mouse and human ESC differentiation systems (Choi et al., 1998; Kennedy et al., 2007). However, the exact position of HBs (BL-CFCs) within the hierarchy of human angiohematopoietic cells and their developmental potential remains unclear. BL colonies were reported from differentiated hESCs at early stages of mesodermal development (Davis et al., 2008; Kennedy et al., 2007) as well as from cells at more advanced stages of differentiation including cells already expressing endothelial markers (Lu et al., 2008; Zambidis et al., 2008). Moreover, two types of HB colonies have been recently described, one with and one without myeloid potential (Kennedy et al., 2007).

Figure 5A:
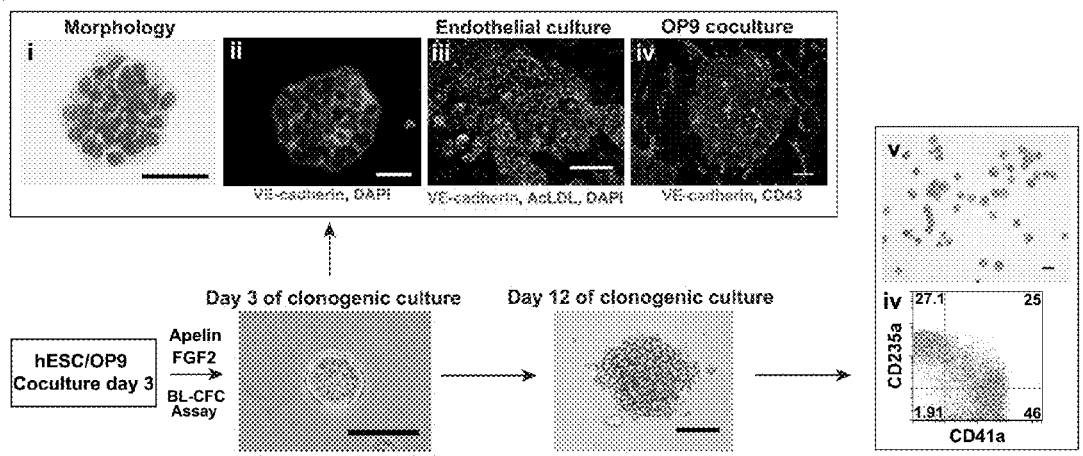
FIG. 5A is a characterization of BL-CFCs and demonstrates hematopoietic and endothelial potential of HB colonies selected at day 3 (core stage; bar=50 μm) and day 12 (mature blast colony; bar=100 μm) of clonogenic culture. Top panels show (i) Wright-stained cytospins (bar=100 μm), (ii) VE-cadherin and AcLDL staining (bar=50 μm), (iii) endothelial culture (bar=100 μm), and (iv) OP9 coculture (bar=100 μm) of HB cores. Left panels show (v) cytospins (bar=20 μm) and (vi) flow cytometric analysis of mature HB colony.
Figure 5B:
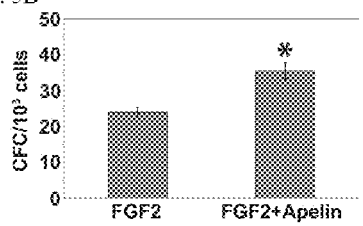
FIG. 5B is a characterization of BL-CFCs and the effect of adding apelin-12 on BL colony formation. Error bars are means±SE of six experiments.

Previously we demonstrated that BL-CFCs arise from day 2-3 $^{EMH}$lin⁻APLNR⁺PDGFRα⁺ (A⁺P⁺) mesodermal population which expresses genes associated with primitive streak and lateral plate/extraembryonic mesoderm development reminiscent of primitive posterior mesoderm (PM) in the embryo (Vodyanik et al., 2010). We showed that BL-CFCs could be detected using serum-free FGF2-containing clonogenic medium (Vodyanik et al., 2010). Here, we also found that the number of BL-CFCs could be increased by adding APLNR ligand apelin-12 to the clonogenic medium (FIG. 5B). Although hematopoietic cytokines are commonly added to BL-CFC clonogenic medium, we avoided their use in our assay to increase its specificity by eliminating false-positive results due to the detection of hematopoietic progenitors. Using optimized BL-CFC-specific assay with FGF2 and apelin-12 we detected BL-CFC activity almost exclusively in day 3 A⁺P⁺ cells (FIG. 5F), indicating that HBs (BL-CFCs) are distinct from day 4 HVMPs and day 5 HEPs and AHPs.

Figure 5C:
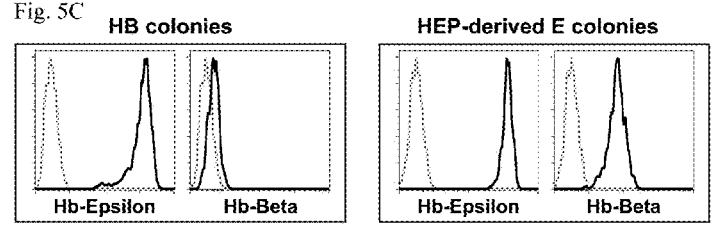
FIG. 5C is a characterization of BL-CFCs and flow cytometric analysis of expression of adult and embryonic hemoglobins in HB colonies and erythroid colonies derived from V$^+$73$^-$235$^-$ HEPs after coculture on OP9.
Figure 5D:
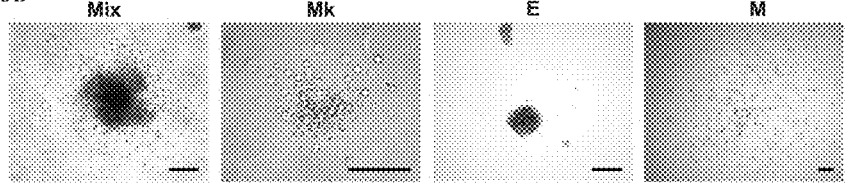
FIG. 5D is a characterization of BL-CFCs and morphology of typical hematopoietic colonies generated from day 12 BL colonies after replating them into H4436 serum-free methylcellulose clonogenic medium containing hematopoietic cytokines; bars=200 μm.
Figure 5E:
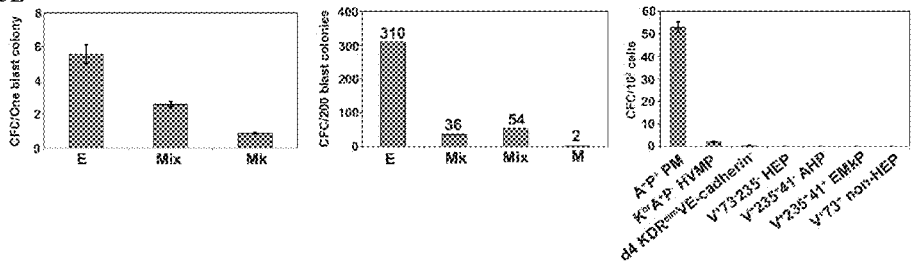
FIG. 5E is a characterization of BL-CFCs and frequency of hematopoietic colonies formed after replating of HB colonies into serum-free hematopoietic CFC medium. Left panel shows results of replating 20 individual colonies; error bars are means±SE of three experiments. Right panel shows results of replating 200 blast colonies.
Figure 5F:
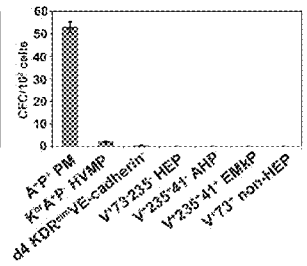
FIG. 5F is a characterization of BL-CFCs and BL-CFC potential of indicated cell subsets detected using FGF2 and apelin 12-containing clonogenic medium. Error bars represent standard error of three experiments.

To characterize the developmental potential of BL-CFCs, we analyzed the mature BL colonies using flow cytometry and hematopoietic CFC assay. As shown in FIG. 5A, HB (BL) colonies collected on day 12 of clonogenic culture consisted almost entirely of CD235a and/or CD41a expressing cells with erythroblast morphology. In contrast to erythroid colonies generated from V⁺73⁻235⁻ HEPs, BL-CFCs expressed no adult β hemoglobin (FIG. 5C). The replating of 20 individual blast colonies into serum-free hematopoietic clonogenic medium demonstrated that they could give rise to erythroid, megakaryocyte, and macrophage colonies, as well as mixed colonies composed of all three cell types (FIGS. 5D and 5E).

When a pool of 200 blast colonies was collected, we were able to detect the same spectrum of hematopoietic CFCs. The spectrum of hematopoietic CFCs was similar when BL-CFCs were replated into standard serum-containing hematopoietic CFC medium, although we observed a reduction in number of erythroid colonies and a slight increase in macrophage colonies (not shown). These results indicate that BL-CFC hematopoietic potential is mostly restricted to primitive cells of erythromegakaryocytic and macrophage lineages.

As previously demonstrated, BL-CFCs represent single cell-derived clonogenic progenitors, which generate hematopoietic cells through the formation of an endothelial intermediate (Lancrin et al., 2009; Vodyanik et al., 2010). This transitional intermediate appears as a core-like structure that forms during the first 3 days of clonogenic culture (FIG. 5A) and distinguishes HB colonies from FGF2-dependent hematopoietic colonies formed from day 5 AHPs (FIG. 12A). HB cores were formed by epithelioid cells, which stained positively for VE-cadherin.

However, in contrast to membranous VE-cadherin expression typically seen in mature endothelial cells, HB cores cells showed predominantly cytoplasmic with limited membranous VE-cadherin expression. When HB cores were cultured in endothelial conditions, up to 95% of them generated typical VE-cadherin⁺ endothelial clusters that were capable of efficient AcLDL incorporation. When HB cores were collected and cultured on OP9 with hematopoietic cytokines, they generated hematoendothelial clusters (FIG. 5A).

Figure 10B:
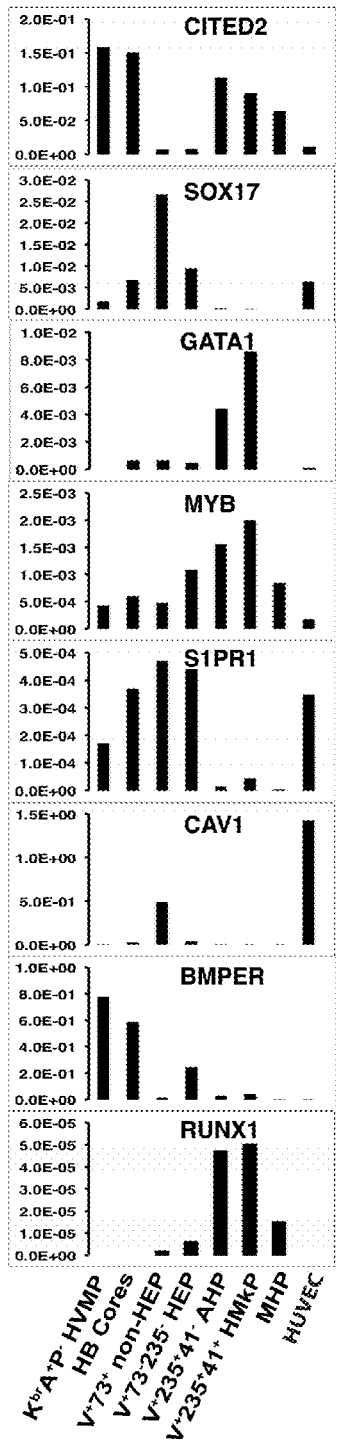
FIG. 10B is an analysis of differentially expressed genes in the day 5 VE-cadherin+ subsets and day 4 HVMPs with quantative RT-PCR analysis of representative transcripts in indicated cell subsets. Scale bars represent a mean of two experiments normalized to RPL13.

Molecular profiling studies demonstrated that HB cores had a gene expression profile very similar to day 5 HEPs, although the HB cores had much lower expression of RUNX1 gene associated with definitive hematopoiesis compared to day 5 HEPs (FIGS. 3A and 10B). Together, these studies indicate that BL-CFCs originate from the more primitive A⁻P⁺ PM and reflect the first wave of yolk sac hematopoiesis, which proceeds through the endothelial intermediate stage with restricted erythroid, megakaryocytic, and macrophage potential.

To find out whether the hematopoietic potential of A⁺P⁺ PM is restricted to primitive HB-derived hematopoiesis or whether these cells contain precursors of definitive angiohematopoietic progenitors, we isolated day 2.5 A⁺P⁺ cells (FIG. 4B) and recultured them on OP9. At this stage, K$^{br}$A⁺P⁻ cells were not detected. As shown in FIG. 12B, A⁺P⁺ cells rapidly expanded on OP9 and generated the entire spectrum of angiohematopoietic and hematopoietic progenitors, which we typically observed in primary hESC/OP9 coculture. These data indicate that A⁺P⁺ PM contains precursors for both primitive and definitive hematopoiesis. Although maturation of primitive angiohematopoietic progenitors was achieved in serum-free semisolid medium in presence of FGF2, stromal factors were essential for the maturation of definitive type angiohematopoietic progenitors from A⁺P⁺ PM.

Hematoendothelial Development from iPSCs

To determine whether other hPSC lines follow similar patterns of hematoendothelial differentiation as we observed with H1 hESC, we analyzed development of newly identified subsets of angiohematopoietic progenitors from transgene-free fibroblast-derived hiPSCs (Yu et al., 2009) and H9 hESCs. As shown in FIG. 13, all examined hPSC lines formed phenotypically and functionally similar subsets of progenitors, including day 4 HVMPs, day 5 HEPs, AHPs, and non-HEPs.

Discussion

During the last decade, significant progress has been made in identifying the major stages of hematopoietic development from hESCs/iPSCs (Kennedy et al., 2007; Vodyanik et al., 2006; Zambidis et al., 2005) and their differentiation toward particular blood lineages (Choi et al., 2009b; Lu et al., 2008; Olivier et al., 2006; Timmermans et al., 2009; Woll et al., 2005). However, the development of cells with hematopoietic reconstitution potential from ESC/iPSCs remains a challenge. Although several studies have shown the bone marrow engraftment of differentiated human ESCs and iPSCs, the engraftment rates were low and mostly restricted to myeloid cells (Ledran et al., 2008; Lu et al., 2009; Narayan et al., 2006; Risueno et al., 2012; Tian et al., 2006; Wang et al., 2005). The most likely explanation for these findings is that in vitro conditions do not support HSC formation from its direct HE precursor. Thus, access to well-defined population of HE cells is essential for developing an in vitro system for the identification of the critical factors that control maturation of engraftable hematopoietic cells from endothelium.

Previous studies demonstrated that cells expressing endothelial molecules differentiated from mouse and human ESCs can generate blood cells (Eilken et al., 2009; Hashimoto et al., 2007; Nishikawa et al., 1998; Vodyanik et al., 2006; Wang et al., 2004). It has been also shown that HE can be prospectively separated from non-HE in mouse ESC cultures based on the activity of Flk1 promoter/enhancer (Hirai et al., 2003). Here we demonstrated for the first time that the CD73 phenotypic marker can be used to separate prospectively HE cells from non-HE progenitors. Importantly, we also found that the VE-cadherin$^+$CD41a$^-$CD45a$^-$ population in hPSC cultures includes CD235a$^+$ (Glycophorin A$^+$) hematopoietic progenitors, which retain angiogenic potential.

Based on these findings we were able to further specify the phenotype of HEPs as VE-cadherin$^+$CD73$^-$CD235a/CD43$^-$ and demonstrate that HEP represented a transient population of endothelial cells emerging immediately after the beginning of endotheliogenesis in hPSC cultures and rapidly declining within next 3 days of differentiation. These HEPs had the potential to generate β-hemoglobin-producing red blood cells and the entire spectrum of myeloid progenitors including pan-myeloid GEMM progenitors, which has been identified within human embryonic tissues but not yolk sac (Hann et al., 1983; Huyhn et al., 1995). Although we and others already demonstrated that CD34$^+$CD43$^+$ progenitors generated in hPSC/OP9 coculture have T and B lymphoid potential (Carpenter et al., 2011; Timmermans et al., 2009; Vodyanik et al., 2005; Vodyanik et al., 2006), further studies will be required to prove that CD34$^+$CD43$^+$ cells with lymphoid potential arise directly from HEPs.

By analyzing the expression of mesodermal markers at stages preceding endotheliogenesis, we identified $^{EMH}$lin$^-$KDR$^{bright}$APLNR$^+$PDGFRα$^{low/-}$ HVMPs as the direct precursors of a definitive type of HEPs. The HVMPs and HEPs required stromal factors for hematopoietic development and were distinct from HBs which arise from day 3 A$^+$P$^+$ PM cells and can be specifically detected in serum-free semisolid medium in the presence of FGF2 and apelin-12. The hematopoietic potential of HB colonies detected using these conditions was mostly restricted to cells of erythromegakaryocytic lineage reflecting the first wave of hematopoiesis observed in the yolk sac. These results are also consistent with mouse studies which demonstrated that Flk1-positive hemangioblastic cells are mainly primitive hematopoietic cells (Fehling et al., 2003). Hematopoietic cells within HB colonies arise through core-forming VE-cadherin$^+$ cells, which in contrast to definitive angiohematopoietic progenitors develop in serum-free medium without stromal support. HB cores have endothelial gene expression profile and potential.

However, our finding that HB cores express intracellular rather than membranous VE-cadherin indicates that they are different from definitive HEPs and may represent distinct type of immature cells of endothelial lineage which are more similar to angioblastic mesodermal cells than to more mature endothelial cells which line already established blood vessels. VE-cadherin$^+$ cells that co-express CD31, CD34, CD105, and TEK endothelial markers were identified within subset of Flk1-positive cells in the extraembryonic mesoderm region during gastrulation and yolk sac blood islands of the E7.0-7.5 mouse embryos (Ema et al., 2006; Yokomizo et al., 2007). These cells are capable to generate endothelial and primitive blood cells. Because HB cores have similar phenotypic and functional characteristics, they could be equivalent to the VE-cadherin$^+$ cells detected within Flk1$^-$ extraembryonic compartment.

The present study revealed a unique population of AHPs expressing VE-cadherin and glycophorin A (CD235a) erythroid marker but lacking CD41a. These AHPs represent multipotential hematopoietic progenitors, which similar to BL-CFCs (HBs) require serum-free conditions and FGF2 for colony formation. However, in contrast to BL-CFCs, the development of colonies from AHPs depends on hematopoietic cytokines and does not proceed through an endothelial core stage.

Another unique feature of AHPs is their angiogenic capability, which is completely lost in CD235a$^+$CD41a$^+$ cells that arise at later stages of differentiation. FGF2- and hematopoietic cytokine-dependent colonies with and without endothelial potential have been described in mouse yolk sac, fetal liver and AGM (He et al., 2010; Yao et al., 2007), indicating that AHPs may have in vivo counterparts. Given the fact that AHP cells express a definitive hematopoiesis transcriptional factor RUNX1 (FIGS. 4 and 12C), and possess erythroid, uni- and multilineage myeloid differentiation potential, they may represent precursors for a transient wave of definitive erythromyeloid hematopoiesis similar to the one described in mouse yolk sac (Palis et al., 1999).

Figure 6:
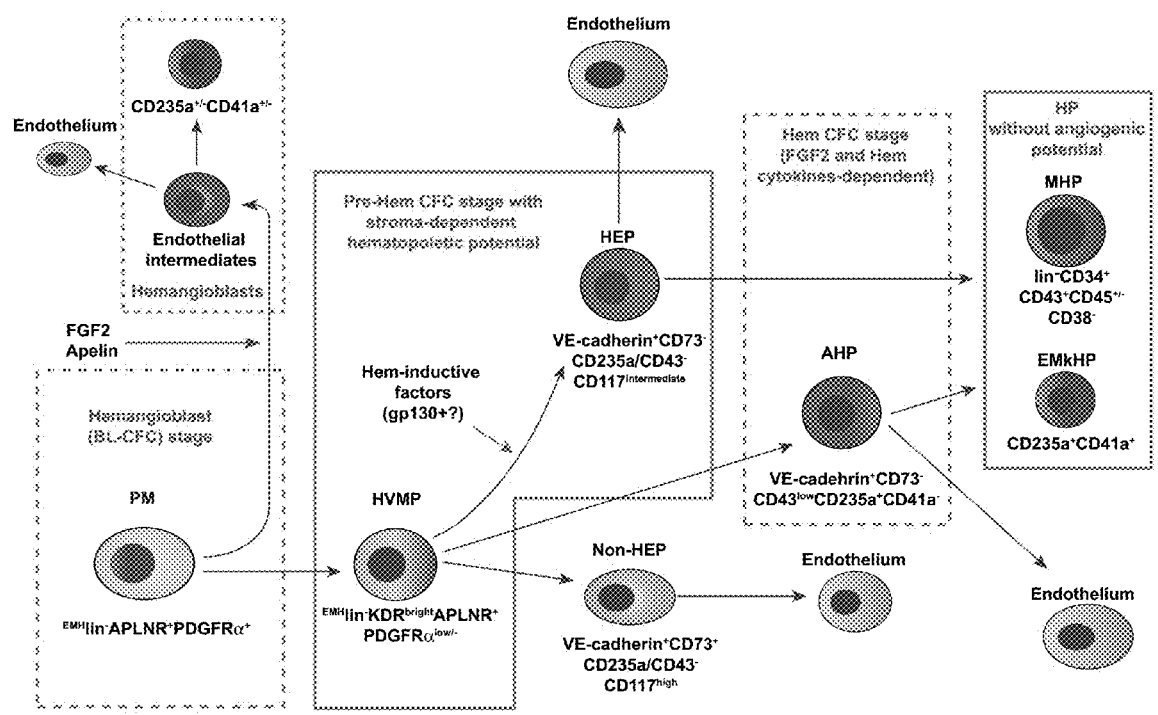
FIG. 6 shows the distinct stages of angiohematopoietic differentiation from hPSCs in coculture with OP9. hESC coculture with OP9 induces mesendodermal differentiation. The first cells with angiohematopoietic potential arise within $^{EMH}$lin$^-$APLNR$^+$PDGFRα$^+$ mesoderm. These cells have the potential to form BL (HB) colonies, which can be specifically detected in serum-free semisolid medium containing FGF2 and apelin. Development of BL colonies proceeds through a core stage at which mesodermal cells form clusters of tightly packed endothelial intermediates (cores). Subsequently, core-forming endothelial cells give rise predominantly to erythromegakaryocytic cells. Advanced mesodermal commitment of hESCs toward hematoendothelial lineage in coculture with OP9 is associated with upregulation of KDR and downregulation of PDGFRα within APLNR$^+$ population, and the development of HVMPs. These cells are highly enriched in bipotential hematoendothelial cluster-forming cells. After gaining VE-cadherin expression, cells gradually acquire endothelial or hematopoietic cell morphology and gene expression profile. The earliest hematopoietic progenitors emerging within VE-cadherin$^+$ population, AHPs, display CD43$^{low}$CD235a$^+$ phenotype and possess endothelial and FGF2-dependent erythromyeloid potential. Expression of CD73 within VE-cadherin$^+$CD235a/CD43$^-$ population discriminates non-HEPs and HEPs. HEPs do not form hematopoietic CFCs in semisolid medium, but are capable of generating the entire spectrum of definitive myeloid cells and β-globin-producing red blood cells when cultured on OP9. Progressive hematopoietic differentiation is associated with upregulation of CD43 expression, acquisition of CD41a and/or CD45 markers, and loss of endothelial potential. Similar pattern of hemoendothelial development is observed from hiPSCs.

In addition, our studies provided important insight on endothelial development from hESCs. Although one commonly held view implies that all endothelial cells in PSC cultures originate from HBs, our current and prior studies (Vodyanik et al., 2010) are in agreement with other studies (Era et al., 2008) that indicate that PSCs give rise to multiple types of endothelial progenitors. Importantly, we demonstrated that emerging endothelial progenitors are multipotent and are able to differentiate into cells of other mesodermal lineages. The first progenitors with endothelial potential, the mesenchymoangioblasts arise from PSCs on day 2 of differentiation and are capable of forming mesenchymal colonies (Vodyanik et al., 2010). HBs capable of generating primitive blood cells through endothelial intermediates in semisolid medium arise one day later. Endothelial intermediates that form HB colonies most likely resemble the yolk sac HE. HEPs that develop by day 5 in hPSC/OP9 coculture express RUNX1, and have the potential to generate multipotential myeloid cells and β-globin producing erythroid cells, and thus resemble definitive-type endothelial progenitors. Non-HEPs were distinctively recognized by the expression of CD73 (FIG. 6).

CD73, also known as 5'-ectonucleotidase, is a glycosylphosphatidylinositol (GPI) linked 70-kDa glycoprotein that produces extracellular adenosine and is abundantly expressed by endothelial cells, MSCs, subsets of peripheral blood lymphocytes, and a variety of other tissues (Delorme et al., 2008; Thomson et al., 1990). CD73 is involved in the regulation of vascular permeability and maintenance of the barrier function, adaptation to hypoxia, ion and fluid transport, and regulation of inflammatory responses in the extracellular milieu (Colgan et al., 2006). Given the physiological significance of CD73, it is likely that expression of this molecule reflects not only differences in developmental potential, but also in the functional properties of HE and non-HE subsets.

Other distinctive features of $CD73^+$ non-HEP were the lack of CD226 hematopoietic marker expression and the strong expression of CD117 (c-KIT). CD117 is known to mark HSCs arising from AGM, and is also found in $CD45^-$ $CD31^-$ circulating endothelial progenitors and cardiac endothelial progenitors (Peichev et al., 2000; Sandstedt et al., 2010; Tallini et al., 2009). The strong expression of CD117 and the lack of hematopoietic potential in $CD73^+$ endothelial cells indicate that these cells represent a population of endothelial progenitors distinct from blood-forming endothelial progenitors and may resemble circulating or tissue-specific endothelial progenitors. These cells also capable of undergoing endothelial-mesenchymal transition.

In conclusion, the identification of distinct subsets of cells with angiohematopoietic potential in our studies provides a hPSC-based platform for identification of molecular determinants of HSC development with a goal to facilitate generation of HSCs from hPSCs.

Maintenance of hPSCs

H1 and H9 hESC lines were obtained from WiCell Research Institute (Madison, Wis.). Transgene-free DF4-3-7T and DF19-9-7T human iPSC cell lines produced using episomal vectors (Yu et al., 2009). All hESC/iPSC lines were maintained in undifferentiated state on irradiated mouse embryonic fibroblasts as described previously (Yu et al., 2007).

hPSC Differentiation in OP9 Coculture hESC/iPSCs were differentiated in coculture with OP9 stromal cells provided by Dr. Toni Nakano (Osaka University, Japan) and depleted of OP9 cells using anti-mouse CD29 antibodies (Serotec) as described (Vodyanik et al., 2010).

Cell Sorting and Analysis of Hematopoietic and Endothelial Potential

The approach and antibodies used for isolation of distinct subsets of progenitors with angiohematopoietic potential is depicted in FIG. 8 and Table 2. VE-cadherin$^+$ or $CD31^+$ cells were isolated from day 5 hESC/OP9 cocultures by positive MACS selection using corresponding FITC-conjugated antibodies and anti-FITC magnetic beads (Miltenyi). MACS separated cells were stained with CD73-PE, CD235a-APC and CD43-APC, and CD41a-PECy7 antibodies and sorted using a FACSARIA cell sorter (BD Biosciences) to select subsets as depicted in FIGS. 1B and 8. To isolate day 4 subsets from hPSC/OP9 cocultures, KDR positive cells were selected by positive MACS selection using KDR-PE antibody (R&D SYSTEMS) and anti-PE magnetic beads (Miltenyi). After labeling with VE-cadherin-APC antibody, $KDR^{bright}$VE-cadherin$^-$, $KDR^{dim}$VEcadherin$^-$ and $KDR^-$ cells were further separated using the FACSARIA sorter. $APLNR^+$ cells were isolated from day 3 hESC/OP9 cocultures by MACS sorting with APLNR-APC antibodies and APC-magnetic beads or FACSARIA sorter after depletion of OP9 with anti-mouse CD29 antibodies as described (Vodyanik et al., 2010). Hematopoietic and endothelial potential of isolated cells was evaluated before and after secondary coculture with OP9 using CFC assay, endothelial culture, and flow cytometry.

Flow Cytometry

Cell surface staining was done using the antibodies listed in Table 1, and 7-aminoactinomycin D (7AAD) for dead cells exclusion and/or TRA-1-85 Abs to select for human cells as described (Vodyanik and Slukvin, 2007). Intracellular staining to determine hemoglobin and vWF expression was performed using FIX&PERM cell permeabilization reagents (CALTAGINVITROGEN).

Hematopoietic Colony-Forming Assay

Hematopoietic clonogenic assays were performed using METHOCULT™ GF+ H4435 complete methylcellulose medium with FBS and SCF, G-CSF, GM-CSF, IL-3, IL-6, EPO cytokines (STEM CELL™ Technologies). Detection CFC potential of VE-cadherin+CD73-CD43lowCD235a+ CD41a- cells was performed using serum-free METHOCULT™ H4236 methylcellulose STEM CELL™ Technologies) with added FGF2 (20 ng/mL), SCF (20 ng/mL), IL3 (10 ng/mL), IL6 (10 ng/mL), and EPO (2 U/mL); i.e., FS36E methylcellulose. Hematopoietic potential of hemangioblast colonies was evaluated by replating them in METHOCULT GF+ H4435, or serum-free METHOCULT H4436 containing SCF, G-CSF, GM-CSF, IL-3, IL-6, EPO cytokines (Stem Cell Technologies).

Colony-Forming Assay for Identification of Hemangioblast BL-CFCs

BL-CFCs were detected using the semisolid colony-forming serum-free medium (CF-SFM) containing 40% ES CULT™ M3120 methylcellulose (2.5% solution in IMDM; STEM CELL™ Technologies), 25% STEM SPAN™ serum-free expansion medium (SFEM; STEM CELL™ Technologies), 25% human endothelial serum-free medium (ESFM; INVITROGEN™), 10% BIT 9500 supplement (STEM CELL™ Technologies), GLUTAMAX™ (1/100 dilution; Invitrogen), EX-CYTER® supplement (1/1000 dilution; Millipore, Billerica, Mass.), 100 µM MTG, 50 µg/ml ascorbic acid and 20 ng/ml basic fibroblast growth factor (FGF2) and apelin-12 (100 ng/ml; Phoenix Pharmaceuticals Inc) as described (Vodyanik et al., 2010).

Endothelial Culture and Assays

To reveal endothelial potential, isolated cell subsets were plated on fibronectin-coated 6-well plates in endothelial serum-free medium (INVITROGEN™) supplemented with 20 ng/mL FGF2, 20 ng/mL EGF (PEPROTECH®), and endothelial cell growth factor (Sigma-Aldrich) at densities indicated in Table 3. Once the cells formed a monolayer (See Table 3), they were evaluated for VE-cadherin expression by immunofluorescence, Ac-LDL uptake, and tube formation. For the acetylated low-density lipoprotein assay (AcLDL), cells were incubated with 10 µg/ml of Alexa594- or Alexa488-conjugated AcLDL (INVITROGEN™) or DiI AcLDL (Biomedical Technologies) for 4 hours at 37° C. and were analyzed by either under fluorescent microscopy or by flow cytometry. Parallel cultures incubated at 4° C. were used as a negative control (AcLDL binding). For vascular tube formation, cells were transferred onto growth factor-reduced MATRIGEL™ (BD Biosciences) and cultured in endothelial medium in presence of 40 ng/ml $VEGF_{165}$ at 37° C. in 5% $CO_2$.

Analysis of Angiohematopoietic Potential

Isolated cells from various subsets were cultured on OP9 in αMEM supplemented with 10% FBS and cytokines SCF (50 ng/ml), TPO (50 ng/ml), IL-3 (10 ng/ml), and IL-6 (20 ng/ml). After 5-6 days of culture on OP9, cells were harvested and analyzed by flow cytometry or stained in situ with rabbit anti-human VE-cadherin in combination with mouse anti-human CD43 and corresponding secondary antibodies and analyzed under fluorescent microscope as described (Vodyanik et al., 2010). For the single cell deposition assay, individual cells were deposited into 96 well plates containing OP9 cells using the FACSARIA™ cell sorter and were cultured for 10-12 days in αMEM supplemented with 10% FBS and cytokines SCF (50 ng/ml), TPO (50 ng/ml), IL-3 (10 ng/ml), and IL-6 (20 ng/ml). Four 96 well plates were deposited with single cells for each subset in three independent experiments. The development of hematopoietic, endothelial, and hematoendothelial clusters from a single cell was analyzed by immunofluorescence with VE-cadherin and CD43 antibodies as previously described (Vodyanik et al., 2010). The frequencies of cells with potential to form hematopoietic, endothelial, or hematoendothelial clusters were calculated as percentages of cluster-containing wells from total number of cell-deposited wells.

Quantitative Real Time PCR (Q-RT-PCR)

Total RNA was extracted from the sorted cell populations using AMBION® RIBOPURE™ Kit (AMBION®) and was subjected to subsequent DNaseI treatment using TURBO DNase™ kit (AMBION®). cDNA synthesis was carried out using ADVANTAGE RT-for-PCR Kit (Clontech). Q-RTPCR analysis was performed for the all the cDNA samples using self-designed specific primers (Table 2) and PLATINUM SYBR® Green qPCR SuperMix-UDG kit (INVITROGEN™). The reactions were run on a MASTERCYCLER® ep realplex thermal cycler (Eppendorf) and expression levels were calculated by minimal cycle threshold values (Ct) normalized to the reference expression of ribosomal protein L13A (RPL13A) in each sample (Pfaffl, 2001).

RNA-Seq Analysis

Total RNA was isolated from the subpopulations cells using RIBOPURE_kit (AMBION®) and were treated with TURBO DNase™ kit (AMBION®). The quality of the total RNA was confirmed by capillary electrophoresis on the Bioanalyzer 2100 (Agilent Technologies). Poly A+ RNAs were linearly amplified using a modified T7 amplification method (Sengupta et al., 2010) to generate highly consistent, strand-specific mRNA-Seq libraries. After cDNA library preparations, the samples were quantitated with the QUBIT® fluorometer (INVITROGEN™) and were then sequenced for forty-two cycles of single-read sequencing on the ILLUMINA® Genome Analyzer IIx. Image analysis and base calling were done with the ILLUMINA® Genome Analyzer Pipeline Software. After quality assessment and adaptor filtering, the raw sequencing reads were then aligned to the annotated 31,147 RefSeq genes (Human hg18 or NCBI36 build) using the Bowtie algorithm by allowing two mismatches (Langmead et al., 2009). At most, 200 alignments were allowed if a read maps to multiple genes (gene multireads) or maps to a single gene but multiple isoforms (isoform multireads). Isoform or gene relative expression levels were estimated and quantified by the RSEM algorithm in terms of "transcripts per million" (tpm) (Li et al., 2010). Hierarchical cluster analyses were carried out with PCC (Pearson correlation coefficient) as the distance metric. The average distance between each cluster pair was used as the basis to merge lower-level clusters into higher-level clusters. To visualize the gene-expression levels, a heat-map was composed using MultiExperiment Viewer v4.2 (http://www.tm4.org) in TM4 package (Saeed et al., 2006). The RNA-Seg data are deposited in the database (accession number).

Statistical Tests

The significance of differences between the mean values was determined by paired Student's t test.

TABLE 1

| Antibodies | | | | |
|---|---|---|---|---|
| Antigen | Flurochrome conjugated | Clone | Source | Cat. No. |
| CD31 | FITC | WM59 | BD Bioscience | 555445 |
| CD31 | PE | WM59 | BD Bioscience | 555446 |
| CD31 | APC | AC128 | Miltenyi Biotec | 130-092-653 |
| CD32 | PE | 3D3 | BD Bioscience | 552884 |
| CD34 | PE | 8G12 | BD Bioscience | 348057 |
| CD41a | PE | HIP8 | BD Bioscience | 555467 |
| CD41a | PE-Cy7 | HIP8 | BD Bioscience | 561424 |
| CD43 | FITC | 1G10 | BD Bioscience | 555475 |
| CD43 | PE | 1G10 | BD Bioscience | 560199 |
| CD43 | APC | 1G10 | BD Bioscience | 560198 |
| CD43 | None | L60 | BD Bioscience | 551457 |
| CD46 | APC | H130 | BD Bioscience | 555485 |
| CD49D | PE | 9F10 | BD Biosciences | 555503 |
| CD54 | PE | HCD54 | Biolegend | 322707 |
| CD79 | PE | AD2 | BD Biosciences | 550257 |
| CD90 | APC | 5E10 | BD Biosciences | 559769 |
| CD93 | PE | VIMD2 | Biolegend | 336107 |
| CD105 | PE | SN6 | GALTAG | MHCD10504 |
| CD117 | PE | YB5.B8 | BD Biosciences | 555714 |
| CD117 | APC | YB5.B8 | BD Biosciences | 550412 |
| CD166 | PE | 3A6 | BD Biosciences | 559263 |
| CD141 | PE | 1A4 | BD Biosciences | 559781 |
| CD143 | PE | BB9 | BD Biosciences | 557928 |
| CD146 | PE | P1H12 | BD Biosciences | 550315 |
| CD151 | PE | 210127 | R&D Systems | FAB1884P |
| CD201 | PE | RCR-252 | BD Biosciences | 557950 |
| CD226 | PE | 11A8 | Biolegend | 338305 |
| CD235a | FITC | GA-R2 (HIR2) | BD Bioscience | 559943 |
| CD235a | PE | GA-R2 (HIR2) | BD Bioscience | 555570 |
| CD235a | APC | GA-R2 (HIR2) | BD Bioscience | 551336 |
| APLNR | APC | 72133 | R&D Systems | FAB856A |
| β Hemoglobin | FITC | 37-8 | Santa Cruz | SC-21757 |
| ε Hemoglobin | FITC | 0900-50 | Fitzgerald | 61C-CR8008M1F |
| CXCR4 | APC | 12G5 | eBioscience | 17-9999-42 |
| Endomucin | None | L10B5 | Dr. D. Vestweber | |

TABLE 1-continued

Antibodies

| Antigen | Flurochrome conjugated | Clone | Source | Cat. No. |
|---|---|---|---|---|
| ESAM | FITC | 408519 | R&D Systems | FAB4204F |
| FLT1 | APC | 49560 | R&D Systems | FAB321A |
| KDR | PE | 89106 | BD Biosciences | 560494 |
| KDR | PE | 89106 | R&D Systems | FAB357P |
| KDR | APC | 89106 | R&D Systems | FAB357A |
| KDR | Alexa Fluor647 | 89106 | BD Biosciences | 560496 |
| PDGFRα | PE | αR1 | BD Biosciences | 556002 |
| TEK | APC | 83715 | R&D Systems | FAB3131A |
| SSEA-3 | PE | MC-631 | Stemgent | 09-0044 |
| SSEA-4 | PE | MC813-70 | Stemgent | 09-0003 |
| TRA-1-60 | PE | TRA-1-60 | Stemgent | 09-0009 |
| TRA-1-81 | PE | TRA-1-81 | Stemgent | 09-0012 |
| TRA-1-85 | FITC | TRA-1-85 | R&D Systems | FAB3195F |
| TRA-1-85 | APC | TRA-1-85 | R&D Systems | FAB3195A |
| VE-cadherin | None | Polyclonal | eBioscience | BMS 158 |
| VE-cadherin | PE | 16B1 | eBioscience | 12-1449 |
| VE-cadherin | FITC | 55-7H1 | BD Bioscience | 560411 |
| VE-cadherin | Alexa Fluor647 | 55-7H1 | BD Bioscience | 5614567 |
| VE-cadherin | APC | 16B1 | eBioscience | 17-1449 |
| vWF | None | 2F2-A9 | BD Biosciences | 555849 |

TABLE 2

Primers used for qRT-PCR

| Gene | Direction | Sequences |
|---|---|---|
| CITED2 | Forward | 5' CCG ACA TCG CGA CAG CGA AGC 3'<br>SEQ ID NO: 1 |
| | Reverse | 5' GCC ATT TCC AGT CCT TCC GTT TTT 3'<br>SEQ ID NO: 2 |
| SOX17 | Forward | 5' GCC AG GGC GAG TCC CGT A 3'<br>SEQ ID NO: 3 |
| | Reverse | 5' GCA TCT TGC TCA ACT CGG CGT TGT GCA 3'<br>SEQ ID NO: 4 |
| GATA1 | Forward | 5' CAC CAG CCC AGG TTA ATC CCC AG 3'<br>SEQ ID NO: 5 |
| | Reverse | 5' ACC CCT GAT TCT GGT GTG GAG GA 3'<br>SEQ ID NO: 6 |
| MYB | Forward | 5' ACG GTC CGA AAC GTT GGT CTG 3'<br>SEQ ID NO: 7 |
| | Reverse | 5' CCC CAG TCT CTT GTG TGC CTG G 3'<br>SEQ ID NO: 8 |
| S1PR1 | Forward | 5' CTT GAG CGA GGC TGC GGT TTC 3'<br>SEQ ID NO: 9 |
| | Reverse | 5' CCA GAC GAA CGC TAG AGG GCG 3'<br>SEQ ID NO: 10 |
| CAV1 | Forward | 5' ACG ACG CGC ACA CCA AGGAG 3'<br>SEQ ID NO: 11 |
| | Reverse | 5' AGC TGG CCT TCC AAA TGC CGT 3'<br>SEQ ID NO: 12 |
| BMPER | Forward | 5' GGT GGC ATG CAG ATA CAT TGG ATA 3'<br>SEQ ID NO: 13 |
| | Reverse | 5' TCC AGA GAA ACA CAT TTC CCA CTC 3'<br>SEQ ID NO: 14 |
| RUNX1 | Forward | 5' TGC AGG AGG AAG ACA CAG CAC CC 3'<br>SEQ ID NO: 15 |
| | Reverse | 5' AAC GTG CAT TCT GAG GGC TGT CAT 3'<br>SEQ ID NO: 16 |
| RPL13 | Forward | 5' CCT GGA GGA GAA GAG GAA AGA GA 3'<br>SEQ ID NO: 17 |
| | Reverse | 5' TTG AGG ACC TCT GTG TAT TTG TCA A 3'<br>SEQ ID NO: 18 |

TABLE 3

Endothelial cultures

| Subset abbreviation | Phenotype | Plating Densities cells/cm² | Monolayer achieved |
|---|---|---|---|
| V+73−235−<br>HEP | VE-cadherin+CD73+CD235a/CD43−<br>CD117$^{intermediate}$ | 1,000 | ~5 days |
| V+73+<br>Non-HEP | VE-cadherin+CD73+CD235a/CD43+<br>CD117$^{high}$ | 1,000 | ~5 days |
| V+235+41−<br>AHP | VE-cadherin+CD73+<br>CD43$^{low}$CD235a+CD41a+CD117+ | 2,000 | ~7 days |
| V+235+41+<br>EMkP | VE-cadherin+CD73+<br>CD43+CD235a+CD41a+ | 2,000 | No growth |

TABLE 3-continued

Endothelial cultures

| Subset abbreviation | Phenotype | Plating Densities cells/cm$^2$ | Monolayer achieved |
|---|---|---|---|
| K$^{br}$A+P+ HVMP | $^{EMH}$lin+KDR$^{bright}$APLNR+PDGFRa$^{low/-}$ | 1,000 | ~5 days |
| N/A | KDRdimVE+cadherin+ | 1,000 | ~5 days |
| N/A | KDR+ | 2,000 | No growth |

TABLE 4

Phenotypic features and definition of subsets with endothelial and/or hematopoietic potential from hPSCs analyzed and characterized in the current study

| Abbreviation | Phenotype | Day of isolation** | Definition |
|---|---|---|---|
| V$^+$73$^-$235$^-$ HEP Cell population D | VE-cadherin$^+$CD73$^-$ CD226$^+$CD235a/CD43$^-$ CD117$^{intermediate}$ | 5 | Hemogenic endothelial progenitors that have primary endothelial characteristics, lacking hematopoietic CFC potential and surface markers, but are capable of generating blood and endothelial cells upon coculture with stromal cells. |
| V$^+$73$^+$ Non-HEP Cell population C | VE-cadherin$^+$CD73$^+$CD226$^-$ CD235a/CD43$^-$CD117$^{high}$ | 5 | Non-hemogenic endothelial progenitors that have all functional and molecular features of endothelial cells, and form endothelial colonies on OP9. |
| V$^+$235$^+$41$^-$ AHP Cell Population E | VE-cadherin$^+$CD73$^-$ CD226$^+$CD43$^{low}$ CD235a$^+$CD41a$^-$CD117$^-$ | 5 | Angiogenic hematopoietic progenitors that possess primary hematopoietic characteristics and FGF2 and hematopoietic cytokine-dependent colony-forming potential in serum-free medium but are capable of generating endothelial cells. |
| V$^+$235$^+$41$^+$ EMkP | VE-cadherin$^+$CD73$^-$ CD43$^+$ CD235a$^+$CD41a$^+$ | 5 | Hematopoietic cells enriched in erythromegakaryocytic progenitors. |
| MHP | lin$^-$ CD34$^+$CD43$^+$CD45$^+$CD38$^-$ | 8 | Multipotential hematopoietic progenitors that lack expression of lineage-specific hematopoietic markers (lin$^-$) and form full spectrum of myeloid colonies in serum-containing semisolid medium supplemented with hematopoietic cytokines |
| K$^{br}$A$^+$P$^-$ HVMP Cell Population A | $^{EMH}$lin$^-$KDR$^{bright}$APLNR$^+$ PDGFRa$^{low/-}$ * | 4 | Hematovascular mesodermal precursor expressing genes associated with lateral plate/extraembryonic mesoderm and angiohematopoietic commitment, but lacking the expression of primitive streak genes. These cells are highly enriched in bipotential cells forming hematoendothelial clusters on OP9. |
| A$^+$P$^+$ PM | $^{EMH}$lin$^-$APLNR$^+$PDGFRa$^+$ * | 3 | Primitive posterior mesoderm enriched in cells expressing typical primitive streak and lateral plate/extraembryonic mesoderm genes. These cells have potential to form FGF2-dependent blast (hemangioblast) colonies in serum-free medium. |

* $^{EMH}$lin$^-$ denotes lack of the expression of CD31, VE-cadherin endothelial, CD73 and CD105 mesenchymal/endothelial cell markers, and CD43 and CD45 hematopoietic cell markers. See also FIG. 8.
**Day of isolation indicates the day of hPSC differentiation in coculture with OP9 at which indicated cell subsets were optimally detected and isolated from cultures.

REFERENCES

Bertrand, J. Y., Chi, N. C., Santoso, B., Teng, S., Stainier, D. Y., and Traver, D. (2010). Haematopoietic stem cells derive directly from aortic endothelium during development. Nature 464, 108-111.

Boisset, J. C., van Cappellen, W., Andrieu-Soler, C., Galjart, N., Dzierzak, E., and Robin, C. (2010). In vivo imaging of haematopoietic cells emerging from the mouse aortic endothelium. Nature 464, 116-120.

Breier, G., Breviario, F., Caveda, L., Berthier, R., Schnurch, H., Gotsch, U., Vestweber, D., Risau, W., and Dejana, E. (1996). Molecular cloning and expression of murine vascular endothelial-cadherin in early stage development of cardiovascular system. Blood 87, 630-641.

Carpenter, L., Malladi, R., Yang, C. T., French, A., Pilkington, K. J., Forsey, R. W., Sloane-Stanley, J., Silk, K. M., Davies, T. J., Fairchild, P. J., et al. (2011). Human induced pluripotent stem cells are capable of B-cell lymphopoiesis. Blood 117, 4008-4011.

Choi, K., Kennedy, M., Kazarov, A., Papadimitriou, J. C., and Keller, G. (1998). A common precursor for hematopoietic and endothelial cells. Development 125, 725-732.

Choi, K., Yu, J., Smuga-Otto, K., Salvagiotto, G., Rehrauer, W., Vodyanik, M., Thomson, J., and Slukvin, I. (2009a). Hematopoietic and endothelial differentiation of human induced pluripotent stem cells. Stem Cells 27, 559-567.

Choi, K. D., Vodyanik, M. A., and Slukvin, I I (2009b). Generation of mature human myelomonocytic cells through expansion and differentiation of pluripotent stem cell-derived lin-CD34+CD43+CD45+ progenitors. J Clin Invest 119, 2818-2829.

Colgan, S. P., Eltzschig, H. K., Eckle, T., and Thompson, L. F. (2006). Physiological roles for ecto-5′-nucleotidase (CD73). Purinergic Signal 2, 351-360.

Corey, D. P., Garcia-Anoveros, J., Holt, J. R., Kwan, K. Y., Lin, S. Y., Vollrath, M. A., Amalfitano, A., Cheung, E. L., Derfler, B. H., Duggan, A., et al. (2004). TRPA1 is a candidate for the mechanosensitive transduction channel of vertebrate hair cells. Nature 432, 723-730.

D'Aniello, C., Lonardo, E., Iaconis, S., Guardiola, O., Liguoro, A. M., Liguori, G. L., Autiero, M., Carmeliet, P., and Minchiotti, G. (2009). G protein-coupled receptor APJ and its ligand apelin act downstream of Cripto to specify embryonic stem cells toward the cardiac lineage through extracellular signal-regulated kinase/p70S6 kinase signaling pathway. Circ Res 105, 231-238.

Davis, R. P., Ng, E. S., Costa, M., Mossman, A. K., Sourris, K., Elefanty, A. G., and Stanley, E. G. (2008). Targeting a GFP reporter gene to the MIXL1 locus of human embryonic stem cells identifies human primitive streak-like cells and enables isolation of primitive hematopoietic precursors. Blood 111, 1876-1884.

de Bruijn, M. F., Ma, X., Robin, C., Ottersbach, K., Sanchez, M. J., and Dzierzak, E. (2002). Hematopoietic stem cells localize to the endothelial cell layer in the midgestation mouse aorta. Immunity 16, 673-683.

Delorme, B., Ringe, J., Gallay, N., Le Vern, Y., Kerboeuf, D., Jorgensen, C., Rosset, P., Sensebe, L., Layrolle, P., Haupt, T., et al. (2008). Specific plasma membrane protein phenotype of culture-amplified and native human bone marrow mesenchymal stem cells. Blood 111, 2631-2635.

Eilken, H. M., Nishikawa, S., and Schroeder, T. (2009). Continuous single-cell imaging of blood generation from haemogenic endothelium. Nature 457, 896-900.

Ema, M., Yokomizo, T., Wakamatsu, A., Terunuma, T., Yamamoto, M., and Takahashi, S. (2006). Primitive erythropoiesis from mesodermal precursors expressing VE-cadherin, PECAM-1, Tie2, endoglin, and CD34 in the mouse embryo. Blood 108, 4018-4024.

Era, T., Izumi, N., Hayashi, M., Tada, S., and Nishikawa, S. (2008). Multiple mesoderm subsets give rise to endothelial cells, whereas hematopoietic cells are differentiated only from a restricted subset in embryonic stem cell differentiation culture. Stem Cells 26, 401-411.

Fehling, H. J., Lacaud, G., Kubo, A., Kennedy, M., Robertson, S., Keller, G., and Kouskoff, V. (2003). Tracking mesoderm induction and its specification to the hemangioblast during embryonic stem cell differentiation. Development 130, 4217-4227.

Ferkowicz, M. J., Starr, M., Xie, X., Li, W., Johnson, S. A., Shelley, W. C., Morrison, P. R., and Yoder, M. C. (2003). CD41 expression defines the onset of primitive and definitive hematopoiesis in the murine embryo. Development 130, 4393-4403.

Hann, I. M., Bodger, M. P., and Hoffbrand, A. V. (1983). Development of pluripotent hematopoietic progenitor cells in the human fetus. Blood 62, 118-123.

Hashimoto, K., Fujimoto, T., Shimoda, Y., Huang, X., Sakamoto, H., and Ogawa, M. (2007). Distinct hemogenic potential of endothelial cells and CD41+ cells in mouse embryos. Dev Growth Differ 49, 287-300.

He, W. Y., Lan, Y., Yao, H. Y., Li, Z., Wang, X. Y., Li, X. S., Zhang, J. Y., Zhang, Y., Liu, B., and Mao, N. (2010). Interleukin-3 promotes hemangioblast development in mouse aorta-gonad-mesonephros region. Haematologica 95, 875-883.

Heinke, J., Wehofsits, L., Zhou, Q., Zoeller, C., Haar, K. M., Helbing, T., Laib, A., Augustin, H., Bode, C., Patterson, C., et al. (2008). BMPER is an endothelial cell regulator and controls bone morphogenetic protein-4-dependent angiogenesis. Circ Res 103, 804-812.

Hirai, H., Ogawa, M., Suzuki, N., Yamamoto, M., Breier, G., Mazda, O., Imanishi, J., and Nishikawa, S. (2003). Hemogenic and nonhemogenic endothelium can be distinguished by the activity of fetal liver kinase (Flk)-1 promoter/enhancer during mouse embryogenesis. Blood 101, 886-893.

Huyhn, A., Dommergues, M., Izac, B., Croisille, L., Katz, A., Vainchenker, W., and Coulombel, L. (1995). Characterization of hematopoietic progenitors from human yolk sacs and embryos. Blood 86, 4474-4485.

Ishida, W., Hamamoto, T., Kusanagi, K., Yagi, K., Kawabata, M., Takehara, K., Sampath, T. K., Kato, M., and Miyazono, K. (2000). Smad6 is a Smad1/5-induced smad inhibitor. Characterization of bone morphogenetic protein-responsive element in the mouse Smad6 promoter. J Biol Chem 275, 6075-6079.

Ivanovs, A., Rybtsov, S., Welch, L., Anderson, R. A., Turner, M. L., and Medvinsky, A. (2011). Highly potent human hematopoietic stem cells first emerge in the intraembryonic aorta-gonad-mesonephros region. J Exp Med 208, 2417-2427.

Jaffredo, T., Gautier, R., Brajeul, V., and Dieterlen-Lievre, F. (2000). Tracing the progeny of the aortic hemangioblast in the avian embryo. Dev Biol 224, 204-214.

Jaffredo, T., Richard, C., Pouget, C., Teillet, M. A., Bollerot, K., Gautier, R., and Drevon, C. (2010). Aortic remodelling during hemogenesis: is the chicken paradigm unique? Int J Dev Biol 54, 1045-1054.

Kataoka, H., Takakura, N., Nishikawa, S., Tsuchida, K., Kodama, H., Kunisada, T., Risau, W., Kita, T., and Nishikawa, S. I. (1997). Expressions of PDGF receptor alpha, c-Kit and Flk1 genes clustering in mouse chromosome 5 define distinct subsets of nascent mesodermal cells. Development, growth & differentiation 39, 729-740.

Kennedy, M., D'Souza, S. L., Lynch-Kattman, M., Schwantz, S., and Keller, G. (2007). Development of the hemangioblast defines the onset of hematopoiesis in human ES cell differentiation cultures. Blood 109, 2679-2687.

Kissa, K., and Herbomel, P. (2010). Blood stem cells emerge from aortic endothelium by a novel type of cell transition. Nature 464, 112-115.

Knezevic, K., Bee, T., Wilson, N. K., Janes, M. E., Kinston, S., Polderdijk, S., Kolb-Kokocinski, A., Ottersbach, K., Pencovich, N., Groner, Y., et al. (2011). A Runx1-Smad6 rheostat controls Runx1 activity during embryonic hematopoiesis. Molecular and cellular biology 31, 2817-2826.

Kojima, H., Kanada, H., Shimizu, S., Kasama, E., Shibuya, K., Nakauchi, H., Nagasawa, T., and Shibuya, A. (2003). CD226 mediates platelet and megakaryocytic cell adhesion to vascular endothelial cells. The Journal of biological chemistry 278, 36748-36753.

Lancrin, C., Sroczynska, P., Stephenson, C., Allen, T., Kouskoff, V., and Lacaud, G. (2009). The haemangioblast generates haematopoietic cells through a haemogenic endothelium stage. Nature 457, 892-895.

Langmead, B., Trapnell, C., Pop, M., and Salzberg, S. L. (2009). Ultrafast and memory-efficient alignment of short DNA sequences to the human genome. Genome Biol 10, R25.

Ledran, M. H., Krassowska, A., Armstrong, L., Dimmick, I., Renstrom, J., Lang, R., Yung, S., Santibanez-Coref, M., Dzierzak, E., Stojkovic, M., et al. (2008). Efficient hematopoietic differentiation of human embryonic stem cells on stromal cells derived from hematopoietic niches. Cell Stem Cell 3, 85-98.

Li, B., Ruotti, V., Stewart, R. M., Thomson, J. A., and Dewey, C. N. (2010). RNA-Seq gene expression estimation with read mapping uncertainty. Bioinformatics 26, 493-500.

Lu, M., Kardel, M. D., O'Connor, M. D., and Eaves, C. J. (2009). Enhanced generation of hematopoietic cells from human hepatocarcinoma cell-stimulated human embryonic and induced pluripotent stem cells. Experimental hematology 37, 924-936.

Lu, S. J., Luo, C., Holton, K., Feng, Q., Ivanova, Y., and Lanza, R. (2008). Robust generation of hemangioblastic progenitors from human embryonic stem cells. Regen Med 3, 693-704.

Macpherson, L. J., Xiao, B., Kwan, K. Y., Petrus, M. J., Dubin, A. E., Hwang, S., Cravatt, B., Corey, D. P., and Patapoutian, A. (2007). An ion channel essential for sensing chemical damage. J Neurosci 27, 11412-11415.

Narayan, A. D., Chase, J. L., Lewis, R. L., Tian, X., Kaufman, D. S., Thomson, J. A., and Zanjani, E. D. (2006) Human embryonic stem cell-derived hematopoietic cells are capable of engrafting primary as well as secondary fetal sheep recipients. Blood 107, 2180-2183.

Nishikawa, S. I., Nishikawa, S., Hirashima, M., Matsuyoshi, N., and Kodama, H. (1998). Progressive lineage analysis by cell sorting and culture identifies FLK1+VE-cadherin+ cells at a diverging point of endothelial and hemopoietic lineages. Development 125, 1747-1757.

North, T., Gu, T. L., Stacy, T., Wang, Q., Howard, L., Binder, M., Marin-Padilla, M., and Speck, N. A. (1999). Cbfa2 is required for the formation of intra-aortic hematopoietic clusters. Development 126, 2563-2575.

North, T. E., de Bruijn, M. F., Stacy, T., Talebian, L., Lind, E., Robin, C., Binder, M., Dzierzak, E., and Speck, N. A. (2002). Runx1 expression marks long-term repopulating hematopoietic stem cells in the midgestation mouse embryo. Immunity 16, 661-672.

Oberlin, E., Tavian, M., Blazsek, I., and Peault, B. (2002). Blood-forming potential of vascular endothelium in the human embryo. Development 129, 4147-4157.

Olivier, E. N., Qiu, C., Velho, M., Hirsch, R. E., and Bouhassira, E. E. (2006). Large-scale production of embryonic red blood cells from human embryonic stem cells. Experimental Hematology 34, 1635-1642.

Palis, J., Robertson, S., Kennedy, M., Wall, C., and Keller, G. (1999). Development of erythroid and myeloid progenitors in the yolk sac and embryo proper of the mouse. Development 126, 5073-5084.

Pardanaud, L., Luton, D., Prigent, M., Bourcheix, L. M., Catala, M., and Dieterlen-Lievre, F. (1996). Two distinct endothelial lineages in ontogeny, one of them related to hemopoiesis. Development 122, 1363-1371.

Peichev, M., Naiyer, A. J., Pereira, D., Zhu, Z., Lane, W. J., Williams, M., Oz, M. C., Hicklin, D. J., Witte, L., Moore, M. A., et al. (2000). Expression of VEGFR-2 and AC133 by circulating human CD34(+) cells identifies a population of functional endothelial precursors. Blood 95, 952-958.

Pfaffl, M. W. (2001). A new mathematical model for relative quantification in real-time RT-PCR. Nucleic Acids Res 29, 2002-2007.

Risau, W., and Flamme, I. (1995). Vasculogenesis. Annu Rev Cell Dev Biol 11, 73-91.

Risueno, R. M., Sachlos, E., Lee, J. H., Lee, J. B., Hong, S. H., Szabo, E., and Bhatia, M. (2012) Inability of human induced pluripotent stem cell-hematopoietic derivatives to downregulate microRNAs in vivo reveals a block in xenograft hematopoietic regeneration. Stem Cells 30, 131-139.

Saeed, A. I., Bhagabati, N. K., Braisted, J. C., Liang, W., Sharov, V., Howe, E. A., Li, J., Thiagarajan, M., White, J. A., and Quackenbush, J. (2006). TM4 microarray software suite. Methods Enzymol 411, 134-193.

Sandstedt, J., Jonsson, M., Lindahl, A., Jeppsson, A., and Asp, J. (2010). C-kit+CD45− cells found in the adult human heart represent a population of endothelial progenitor cells. Basic Res Cardiol 105, 545-556.

Sengupta, S., Ruotti, V., Bolin, J., Elwell, A., Hernandez, A., Thomson, J., and Stewart, R. (2010). Highly consistent, fully representative mRNA-Seq libraries from ten nanograms of total RNA. Biotechniques 49, 898-904.

Shalaby, F., Ho, J., Stanford, W. L., Fischer, K. D., Schuh, A. C., Schwartz, L., Bernstein, A., and Rossant, J. (1997). A requirement for Flk1 in primitive and definitive hematopoiesis and vasculogenesis. Cell 89, 981-990.

Shibuya, A., Campbell, D., Hannum, C., Yssel, H., Franz-Bacon, K., McClanahan, T., Kitamura, T., Nicholl, J., Sutherland, G. R., Lanier, L. L., et al. (1996). DNAM-1, a novel adhesion molecule involved in the cytolytic function of T lymphocytes. Immunity 4, 573-581.

Tallini, Y. N., Greene, K. S., Craven, M., Spealman, A., Breitbach, M., Smith, J., Fisher, P. J., Steffey, M., Hesse, M., Doran, R. M., et al. (2009). c-kit expression identifies cardiovascular precursors in the neonatal heart. Proceedings of the National Academy of Sciences of the United States of America 106, 1808-1813.

Taoudi, S., and Medvinsky, A. (2007). Functional identification of the hematopoietic stem cell niche in the ventral domain of the embryonic dorsal aorta. Proc Natl Acad Sci USA 104, 9399-9403.

Thomson, L. F., Ruedi, J. M., Glass, A., Moldenhauer, G., Moller, P., Low, M. G., Klemens, M. R., Massaia, M., and Lucas, A. H. (1990). Production and characterization of monoclonal antibodies to the glycosyl phosphatidylinositol-anchored lymphocyte differentiation antigen ecto-5'-nucleotidase (CD73). Tissue Antigens 35, 9-19.

Tian, X., Woll, P. S., Morris, J. K., Linehan, J. L., and Kaufman, D. S. (2006). Hematopoietic engraftment of human embryonic stem cell-derived cells is regulated by recipient innate immunity Stem Cells 24, 1370-1380.

Timmermans, F., Velghe, I., Vanwalleghem, L., De Smedt, M., Van Coppernolle, S., Taghon, T., Moore, H. D., Leclercq, G., Langerak, A. W., Kerre, T., et al. (2009). Generation of T cells from human embryonic stem cell-derived hematopoietic zones. J Immunol 182, 6879-6888.

Vodyanik, M. A., Bork, J. A., Thomson, J. A., and Slukvin, I I (2005). Human embryonic stem cell-derived CD34+ cells: efficient production in the coculture with OP9 stromal cells and analysis of lymphohematopoietic potential. Blood 105, 617-626.

Vodyanik, M. A., Thomson, J. A., and Slukvin, I I (2006). Leukosialin (CD43) defines hematopoietic progenitors in human embryonic stem cell differentiation cultures. Blood 108, 2095-2105.

Vodyanik, M. A., and Slukvin, I I (2007). Hematoendothelial differentiation of human embryonic stem cells. Curr Protoc Cell Biol Chapter, Unit 23.26.

Vodyanik, M. A., Yu, J., Zhang, X., Tian, S., Stewart, R., Thomson, J. A., and Slukvin, I I (2010). A mesoderm-derived precursor for mesenchymal stem and endothelial cells. Cell Stem Cell 7, 718-729.

Wang, L., Li, L., Shojaei, F., Levac, K., Cerdan, C., Menendez, P., Martin, T., Rouleau, A., and Bhatia, M. (2004). Endothelial and hematopoietic cell fate of human embryonic stem cells originates from primitive endothelium with hemangioblastic properties. Immunity 21, 31-41.

Wang, L., Menendez, P., Shojaei, F., Li, L., Mazurier, F., Dick, J. E., Cerdan, C., Levac, K., and Bhatia, M. (2005). Generation of hematopoietic repopulating cells from human embryonic stem cells independent of ectopic HOXB4 expression. J Exp Med 201, 1603-1614. Epub 2005 May 1609.

Woll, P. S., Martin, C. H., Miller, J. S., and Kaufman, D. S. (2005). Human embryonic stem cell-derived NK cells acquire functional receptors and cytolytic activity. J Immunol 175, 5095-5103.

Xia, X., Ayala, M., Thiede, B. R., and Zhang, S. C. (2008). In vitro- and in vivo-induced transgene expression in human embryonic stem cells and derivatives. Stem Cells 26, 525-533.

Xu, M. J., Matsuoka, S., Yang, F. C., Ebihara, Y., Manabe, A., Tanaka, R., Eguchi, M., Asano, S., Nakahata, T., and Tsuji, K. (2001). Evidence for the presence of murine primitive megakaryocytopoiesis in the early yolk sac. Blood 97, 2016-2022.

Yao, H., Liu, B., Wang, X., Lan, Y., Hou, N., Yang, X., and Mao, N. (2007). Identification of high proliferative potential precursors with hemangioblastic activity in the mouse aorta-gonad-mesonephros region. Stem Cells 25, 1423-1430.

Yokomizo, T., and Dzierzak, E. (2010). Three-dimensional cartography of hematopoietic clusters in the vasculature of whole mouse embryos. Development 137, 3651-3661.

Yokomizo, T., Takahashi, S., Mochizuki, N., Kuroha, T., Ema, M., Wakamatsu, A., Shimizu, R., Ohneda, O., Osato, M., Okada, H., et al. (2007). Characterization of GATA-1(+) hemangioblastic cells in the mouse embryo. The EMBO journal 26, 184-196.

Yu, J., Hu, K., Smuga-Otto, K., Tian, S., Stewart, R., Slukvin, I I, and Thomson, J. A. (2009). Human induced pluripotent stem cells free of vector and transgene sequences. Science 324, 797-801.

Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al. (2007). Induced pluripotent stem cell lines derived from human somatic cells. Science 318, 1917-1920.

Zambidis, E. T., Peault, B., Park, T. S., Bunz, F., and Civin, C. I. (2005). Hematopoietic differentiation of human embryonic stem cells progresses through sequential hematoendothelial, primitive, and definitive stages resembling human yolk sac development. Blood 106, 860-870.

Zambidis, E. T., Soon Park, T., Yu, W., Tam, A., Levine, M., Yuan, X., Pryzhkova, M., and Peault, B. (2008). Expression of angiotensin-converting enzyme (CD143) identifies and regulates primitive hemangioblasts derived from human pluripotent stem cells. Blood 112, 3601-3614.

Zovein, A. C., Hofmann, J. J., Lynch, M., French, W. J., Turlo, K. A., Yang, Y., Becker, M. S., Zanetta, L., Dejana, E., Gasson, J. C., et al. (2008). Fate tracing reveals the endothelial origin of hematopoietic stem cells. Cell Stem Cell 3, 625-636.

We claim:

1. A cell population, comprising:
a purified population of human hemogenic endothelial progenitors, which express VE-cadherin, but do not express CD73, CD235a, and CD43; and a population of OP-9 stromal cells, wherein the progenitors were generated from human pluripotent stem cells wherein the OP-9 stromal cells induced hematoendothelial differentiation of the pluripotent stem cells, and wherein the purified population of human hemogenic endothelial progenitors is at least 94% pure.

2. The cell culture of claim 1 comprising a purified population of the human hemogenic endothelial progenitors which express VE-cadherin, but do not express CD73, CD235a, and CD43 wherein the purified population is at least 98% pure.

3. A cell population, comprising:
a 94% pure population of human hemogenic endothelial progenitors, which express VE-cadherin, but do not express CD73, CD235a, and CD43 wherein the progenitors are obtained by a method comprising the steps of:
a) culturing pluripotent stem cells with OP9 stromal cells so that hematoendothelial differentiation occurs, and
b) sorting the cultured cells of step a) by cell markers selected from the group consisting of VE-cadherin, CD31, CD235a, CD73, CD43 and CD41 a such that a 94% purified cell population of human hemogenic endothelial progenitors is obtained.

4. The cell population of claim 3, wherein the cell population is 98% pure population of human hemogenic endothelial progenitors.

* * * * *

UNITED STATES PATENT AND TRADEMARK OFFICE
CERTIFICATE OF CORRECTION

PATENT NO. : 10,260,047 B2
APPLICATION NO. : 14/955760
DATED : April 16, 2019
INVENTOR(S) : Igor I Slukvin et al.

Page 1 of 1

It is certified that error appears in the above-identified patent and that said Letters Patent is hereby corrected as shown below:

In the Specification

Column 18, Line 30, "$A^-P^+$" should be --$A^+P^+$--.

Column 20, Line 13, "$Flk1^-$" should be --$Flk1^+$--.

Column 21, Line 33, "Dr. Toni Nakano" should be --Dr. Toru Nakano--.

Column 24, Table 1, Cat. No. column, Line 3, "130-092-653" should be --130-092-652--.

Column 25, Table 1, Cat. No. column, Line 6, "560496" should be --560495--.

Column 25, Table 2, Sequences column, Line 6, "AG" should be --AAG--.

Column 25, Table 2, Sequences column, Line 17, "ACG" should be --ACT--.

Column 26, Table 2, Sequences column, Line 1, "AGGAG" should be --AGG AG--.

Column 26, Table 2, Sequences column, Line 11, "AGG AGG" should be --AGGAGG--.

Column 29, Line 27, "Haupt" should be --Haupl--.

Column 29, Line 66, "Haar" should be --Baar--.

Signed and Sealed this
Eighteenth Day of June, 2019

Andrei Iancu
*Director of the United States Patent and Trademark Office*